(12) United States Patent
Chaudhuri

(10) Patent No.: US 11,077,035 B2
(45) Date of Patent: Aug. 3, 2021

(54) HAIR TREATMENT COMPOSITIONS AND METHODS

(71) Applicant: SYTHEON LIMITED, Boonton, NJ (US)

(72) Inventor: Ratan K Chaudhuri, Lincoln Park, NJ (US)

(73) Assignee: SYTHEON LIMITED, Boonton, NJ (US)

( * ) Notice: Subject to any disclaimer, the term of this patent is extended or adjusted under 35 U.S.C. 154(b) by 0 days.

(21) Appl. No.: 16/059,425

(22) Filed: Aug. 9, 2018

(65) Prior Publication Data

US 2019/0046423 A1    Feb. 14, 2019

Related U.S. Application Data

(60) Provisional application No. 62/544,433, filed on Aug. 11, 2017.

(51) Int. Cl.

| | | |
|---|---|---|
| *A61K 8/35* | (2006.01) | |
| *A61K 8/36* | (2006.01) | |
| *A61K 8/37* | (2006.01) | |
| *A61Q 5/00* | (2006.01) | |
| *A61Q 5/02* | (2006.01) | |
| *A61Q 5/08* | (2006.01) | |
| *A61Q 5/12* | (2006.01) | |
| *A61Q 17/04* | (2006.01) | |

(52) U.S. Cl.
CPC .................. *A61K 8/35* (2013.01); *A61K 8/36* (2013.01); *A61K 8/37* (2013.01); *A61Q 5/002* (2013.01); *A61Q 5/004* (2013.01); *A61Q 5/02* (2013.01); *A61Q 5/08* (2013.01); *A61Q 5/12* (2013.01); *A61K 2800/4322* (2013.01); *A61K 2800/51* (2013.01); *A61K 2800/882* (2013.01); *A61K 2800/884* (2013.01); *A61Q 17/04* (2013.01)

(58) Field of Classification Search
CPC ... A61K 8/35; A61K 8/37; A61K 8/36; A61K 2800/884; A61K 2800/882; A61K 2800/51; A61K 2800/4322; A61Q 5/12; A61Q 5/08; A61Q 5/02; A61Q 5/004; A61Q 5/002; A61Q 17/04
See application file for complete search history.

(56) References Cited

U.S. PATENT DOCUMENTS

| | | | |
|---|---|---|---|
| 3,708,540 A | | 1/1973 | Yokotani et al. |
| 4,493,823 A | * | 1/1985 | Moller .................. A61Q 19/00 424/70.8 |
| 5,853,705 A | | 12/1998 | Nakayama et al. |
| 8,414,870 B2 | | 4/2013 | Chaudhuri |
| 8,617,528 B2 | | 12/2013 | Chaudhuri |
| 8,765,101 B2 | | 7/2014 | Marion et al. |
| 2008/0305059 A1 | | 12/2008 | Chaudhuri |
| 2012/0141394 A1 | | 6/2012 | Chaudhuri |
| 2012/0141395 A1 | | 6/2012 | Chaudhuri |
| 2013/0315843 A1 | * | 11/2013 | Haught .................... A61K 8/41 424/48 |
| 2015/0174033 A1 | | 6/2015 | Herrmann et al. |
| 2015/0182431 A1 | * | 7/2015 | Chaudhuri ............... A61K 8/35 424/70.1 |
| 2016/0256368 A1 | | 9/2016 | Samthanam et al. |

FOREIGN PATENT DOCUMENTS

| | | |
|---|---|---|
| EP | 0797984 A2 | 1/1997 |
| WO | 2012/131072 A1 | 10/2012 |
| WO | 2013/176897 A2 | 11/2013 |

OTHER PUBLICATIONS

Hamada et al. (JP2000178140A English Machine Translation) (Year: 2000).*
Kawasaki (JP2003137758A English Machine Translation) (Year: 2003).*
International Search Report and Written Opinion for PCT/US2018/45970, Int'l PCT equivalent to instant application, dated Oct. 3, 2018.
Extended European Search Report dated Apr. 14, 2021 with respect to EP 18188443266, corresponds to the instant application.
Zaugg, HE et. al., "Cation and Solvent Effects on the Ultraviolet Spectra of Alkali Salts of Phenols and Enols", J, American Chemical Soc., Amer. Chem. Soc., US, vol. 87, No. 9, May 1, 1965, pp. 1857-1866.
Euhara, K. et. al., "The Metal Ion Catalyzed Alcoholysis of Beta-dicarbonyl Compounds", Bulletin of the Chemical Society of Japan, vol. 49, No. 2, Jan. 1, 1976, pp. 493-498.

\* cited by examiner

*Primary Examiner* — Aradhana Sasan
*Assistant Examiner* — Quanglong N Truong
(74) *Attorney, Agent, or Firm* — IP&L Solutions; Edward K Welch, II

(57) ABSTRACT

The present invention is directed to the hair care treatment compositions, including pre- and post-treatment compositions, containing select aryl alkanone compounds as quenching and/or chelating agents.

31 Claims, No Drawings

HAIR TREATMENT COMPOSITIONS AND METHODS

RELATED APPLICATIONS

The present application claims the benefit of U.S. Provisional Patent Application No. 62/544,433 filed Aug. 11, 2017, entitled "Hair Treatment Compositions and Methods," the contents of which are hereby incorporated herein by reference in their entirety.

FIELD OF THE INVENTION

The present invention relates to hair care compositions comprising one or more aryl alkanone compounds and methods for reducing hair damage caused by UV-induced or environmental pollution-induced oxidative stress. These compositions reduce and/or aid in reducing oxidative damage sustained by hair fibers during bleaching, repeated shampooing, dyeing, perming or other oxidative treatments as well as from environmental pollution and swimming, especially repetitive swimming, in chemically treated pools. These compositions according to the present invention are also found to provide excellent color evenness and color protection and reduce scalp itching in those compositions employed for altering/preserving hair coloration.

BACKGROUND

Sunlight on human hair causes photo-degradation. This results in bleaching due to melanin oxidation through free radicals and/or non-radical species such as singlet oxygen and induces keratin impairment. UV radiation causes an increase in protein degradation, lipid peroxidation, tryptophan degradation and free radicals formation in hair (E Fernández et al., Journal of Photochemistry and Photobiology B: Biology, Photodamage determination of human hair, 106(5):101-106, 2012). Melanins are the main hair chromophores, conferring more than a beautiful and wide scenario of colors and also exerting a protective role against solar radiation. However, under certain circumstances these pigments can engage in excited-state reactions, damaging themselves and the surrounding tissues (D. Severino et al., Singlet Oxygen in Hair, Chapter 38 in Singlet Oxygen: Applications in Biosciences and Nanosciences, Volume 2, Editors: S Nonell, C Flors, 2016).

Visible light also causes hair damage. Irradiation of hair shafts with light of $\lambda_{ex}$>400 nm changed their properties by degrading the melanin (O. Chiarelli-Neto et al. Free Radical Biology and Medicine, Generation and suppression of singlet oxygen in hair by photosensitization of melanin, 51(6): 1195-1202, 2011). Formation of C3 hydroperoxides in the melanin indole groups was proven by $^1$H NMR. After 532-nm excitation, all hair shafts presented the characteristic $^1O_2$ emission ($\lambda_{em}$=1270 nm), whose intensity varied inversely with the melanin content. $^1O_2$ lifetime was also shown to vary with hair type, being five times shorter in black hair than in blond hair, indicating the role of melanin as a $^1O_2$ suppressor. Both eumelanin and pheomelanin were shown to produce and to suppress $^1O_2$, with similar efficiencies. The higher amount of $^1O_2$ generated in blond hair and its longer lifetime is consistent with the stronger damage that light exposure causes in blond hair. Formation and suppression of $^1O_2$ in hair by photosensitization of melanin with visible light causes deleterious effects on hair and scalp. One approach that can be taken to reduce the formation of singlet oxygen or free radicals is by selecting a singlet oxygen quencher. Quenchers are non-sacrificing molecule whereas scavengers (antioxidant) are sacrificing molecule. Therefore, quenchers are expected to be long-lasting and more effective than conventional antioxidant. The importance of singlet oxygen in producing reactive oxygen species can be depicted in the following scheme:

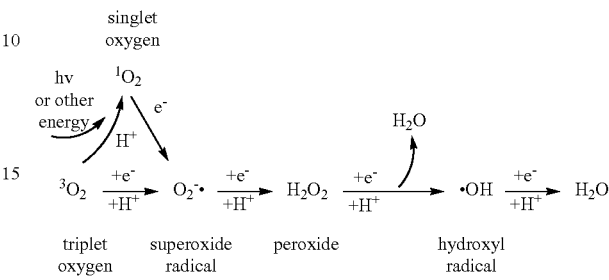

Of course, hair damage is not solely due to light exposure. Minerals such as calcium, magnesium and copper hold on to one's hair every time one washes it with tap water. Calcium and magnesium are relatively benign; copper is not. In the highly alkaline environment of ammonia-based hair dyes (normally a pH of 10 or 11), copper can react with hydrogen peroxide to form highly reactive hydroxyl radicals which markedly affect, in an adverse manner, hair and the scalp. In this respect, it is to be recalled that there are two key reactive species in permanent hair color: the peroxyl anion (HOO$^-$) and the hydroxyl radical (HO$^-$). While HOO$^-$ has some damaging side effects, it is the species that is responsible for the desired changes to hair color. The HO$^-$ radical, on the other hand, is an undesired by-product of a reaction between $H_2O_2$ and metal ions, especially copper. It does not contribute to the development of color but does contribute, significantly so, to hair damage. The elimination of this unnecessary free radical can significantly reduce hair damage without compromising hair colorant performance. One approach taken to reduce the formation of these free radicals is by eliminating the exposure to metal ions; however, current efforts are marginal at best in performance.

As noted, repeated treatment or exposure to oxidative treatments and compositions, especially dyeing, can strain and gradually destroy the hair cuticle—leaving hair harder to control. Consequently, determined brushers become unwitting accomplices in destroying more of the unstable shingle-like cells through the abrasive action of brushing. With less of the cuticle to stop them, the radicals are free to attack the protein fibers within the cortex of the hair by forcing apart their structural supports and fraying their ends. Hence, those nasty split ends.

It's a bit of a vicious cycle. But, even if one doesn't color their hair, copper in other hair treatment compositions, including shampoos, perms, conditioners, sunscreens, hair restorative compositions as well as normal tap water and pool water accumulates in the hair. With every exposure or treatment, the hydroxyl radicals attack the hair's waterproofing layer and make it increasingly porous, allowing more and more copper to get in during the next exposure or treatment. Those who also color their hair merely compound the problem and, in fact, end up with significant accumulation of copper, thereby further compounding the damage.

A number of strategies and efforts have been undertaken to stop this buildup. One strategy is to effectively take out the mineral by binding it to something else. However, most binding materials are not selective or, if selective, are selective for multiple minerals. With far more calcium and other minerals present in oxidative treatment compositions and, more significantly, water, that binding compound would have to be very selective. For example, there is 10 to 100 times more calcium than copper present in typical tap water and, as a result, in hair as well. If one selected a binding agent that bound or reacted with both calcium and copper, it would react with all or essentially all of the calcium before it saw any of the copper.

Various studies have identified 'Sensitive Scalp Syndrome' resulting from exposure to increasing levels of air pollution including particulate matter, dust, smoke, nickel, lead and arsenic, sulfur dioxide, nitrogen dioxide, ammonia and polycyclic aromatic hydrocarbons (PAH) which settle on the scalp and hair. This effect is proliferated in environments having indoor air conditioning since the air is circulated and volatile organic compounds (VOC) released from various sources, e.g., compounds which bloom from substrates, air fresheners, perfumes, etc., build up/become more concentrated and, likewise, settle on the scalp and hair. These pollutants then migrate into the dermis, transepidermally, and through the hair follicle conduit, leading to oxidative stress and hair loss [R Rajput, Understanding Hair Loss due to Air Pollution and the Approach to Management. Hair Ther Transplant 5:133. 2015; doi:10.4172/21670951.10001.33; L Misery et al., Sensitive scalp: does this condition exist? An epidemiological study, Contact Dermatitis, 58: 234-238, 2008]

Fabio Rinaldi performed a study in the city of Milan, Italy in which he studied and documented the effects of pollution on human hair: the study was published and entitled 'What your hair breaths' [F Rinaldi F, Pollution, scalp and hair transplants. Hair Transplant Forum International 18: 227, 2008]. His study involved conducting a scalp analysis of 300 volunteers from July 2007 to April 2008 to assess the yearly average exposures. The concentration and deposition of particulate matter and heavy metals on the hair was one and half times more than levels in the air and deposition on the scalp was double the levels in the air. [See also C Saint-Martory C et al., Sensitive skin is not limited to the face, Br J Dermatol, 158:130-133, 2008]. Correlating these findings to other areas and cities one can readily appreciate the significance of the problem. For example, the pollution in most Indian and Chinese metros is many times higher than the levels in Milan [See e.g., [http://mpcb.gov.in/envtdata; http://www.dpcc.delhigovt.nic.in/Air40.html] Additionally, traffic pollution has been a known cause for respiratory and skin ailments, conditions that involve the same inflammatory processes that affect hair follicles as well [V Morgenstern et al., Atopic diseases, allergic sensitization, and exposure to traffic-related air pollution in children. Am J Respir Crit Care Med, 177: 1331-1337, 2008].

In following, Philpott demonstrated that pollution levels increase oxidative stress on hair follicle cells, leading to increased hair shedding, similar to the mechanism seen in persons suffering from androgenic alopecia [A W Bahta et al., Premature senescence of balding dermal papilla cells in vitro is associated with p16(INK4a) expression, J Invest Dermatol, 128: 1088-1094, 2008]. Accordingly, it is believed that pollution induced hair loss mimics androgenic alopecia and may be difficult to distinguish clinically unless suspected and confirmed by the treating doctor [http://www.omicsgroup.org/journals/understanding-hair-loss-due-to-air-pollution-and-the-approach-to-management-2167-0951-1000133.php?aid=47705]

Although EDTA is a well-known chelator and is widely used in lotions, creams, shampoos, conditioners, bleaching and dyeing compositions, and the like; it displays very little benefit, if any, in addressing hair damage, especially in terms of addressing oxidative effects, because it actually enhances oxidative damage by the following reaction:

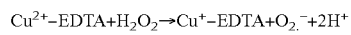

$$Cu^{2+}-EDTA+H_2O_2 \rightarrow Cu^+-EDTA+O_2^{\cdot -}+2H^+$$

(Chaudhuri R K & Puccetti G, Transition Metal-Induced Oxidation: Implications for Skin Care Products, C&T, 117 (9), p.43-56, 2002).

Various attempts have been undertaken and proposed to protect one's hair from damage due to oxidative conditions and exposures instead of merely concealing it. For example, U.S. Pat. No. 4,138,478 discloses compositions for changing the color of hair by the action (direct or indirect) of compounds therein which release nascent oxygen. These compositions are said to do less harm to the hair, as compared to other then state of the art coloring compositions, when they are modified to contain select water-soluble 3-amino-1-hydroxypropane-1,1-diphosphonic compounds, which may be in the form of a free acid or water-soluble salt or a partial ester. It is asserted that hair which is pre-treated with one of the mentioned diphosphonic compounds is at least partially protected against the action of nascent oxygen. According to this patent, "the diphosphonic compound is substantively adsorbed by the hair and acts to hinder degradation of the hair by nascent oxygen which is either present therewith or which is subsequently added."

The use of other phosphonic and diphosphonic compounds have also been found to offer protective properties to hair. For example, the use of hydroxyethane-1,1 diphosphonic acid (HEDP) and ethylenediaminetetramethylene phosphonic acid (EDTMP) are disclosed at low levels in U.S. Pat. Nos. 3,202,579 and 3,542,918, respectively.

Similarly, U.S. Pat. No. 5,100,436 discloses a method of dyeing hair wherein the hair is pretreated with an aqueous solution containing select metal-chelate complexes and then dyed with an oxidative dye mixture. The use of catalytic amounts of select transition metal ions complexed with dipyridyl or o-phenanthroline chelating agents (0.001 to 0.1% by weight of the solution) allows for a reduction in the time of exposure to the dye, thus reducing the damage caused by the oxidizing agent.

U.S. Pat. No. 5,635,167 discloses a process for the removal of exogenous minerals which have become attached to human hair or keratin fiber. The process includes the steps of (i) contacting at least one chelating agent selected from the group consisting of amino acid-type, polyphosphate-type and phosphonate-type agents with the human hair or keratin fiber, (ii) maintaining contact between the chelating agent and the human hair or keratin fiber for a period of time sufficient to permit the chelating agent to complex with the exogenous minerals, thereby removing at least a portion of the attached minerals, and (iii) rinsing the chelating agent, with the chelated mineral, from the hair or keratin fiber. This process is said to be enhanced when the pH is adjusted to a range of between 4 and 9, preferably 5 and 8. The chelating agent is added at a concentration of 4 to 25% by weight, preferably 5 to 20% by weight. In a preferred case, the chelating agent is selected from the group consisting of a salt of ethylenediaminetetraacetic acid, a salt of hydroxyethyl-ethylene-diaminetriacetic acid, a salt of diethylenetriaminepentaacetic acid, a salt of nitrilotriacetic acid and a salt of tripolyphosphate, preferably the sodium salt. The chelating agents used are preferably blends of chelating agents.

U.S. Pat. No. 6,013,250 discloses hair treatment compositions which are said to provide an excellent finishing effect and superior protection against environmental, chemical, and grooming-associated damage. These treatment compositions comprise hydrolyzed protein having an abundance of anionic amino acids and, in particular, sulphur containing amino acids, as well as divalent cationic compounds. It is said that the anionic components of the hydrolyzed protein effectively bind to the hair by means of cationic bridges. While bound to the hair, the sulfur containing amino acids in the hydrolyzed protein serve as "decoys" for the effects of a variety of damaging agents.

U.S. Pat. No. 7,179,302 discloses that ethylenediamine-N,N'-disuccinic acid (EDDS), as well as derivatives and salts thereof, have little attraction for calcium but are effective chelating agents for copper, thereby leaving it unavailable for radical making. Preferred salts include the alkali metal, alkaline earth metal, ammonium and substituted ammonium salts (e.g. monoethanolammonium, diethanolammonium, and triethanolammonium). It is said that these compounds reduce the oxidative damage sustained by keratinous fibers, such as hair, during bleaching, dyeing, perming or other oxidative treatments.

U.S. Pat. No. 7,186,275 discloses hair care compositions comprising specific chelating agents and the use thereof for reducing oxidative hair damage during oxidative treatments of hair such as bleaching, oxidative dyeing or perming. Suitable chelating agents include diamine-N,N'-dipolyacids and monoamine monoamide-N,N'-dipolyacids.

WO97/24106 discloses hair coloring compositions comprising a water soluble peroxygen-bleach, a bleaching aid selected from organic peroxyacid bleach precursors and preformed organic peroxyacids, and one or more hair coloring agents. Various chelating agents are disclosed as optional ingredients and exemplified in hair care compositions at 0.1% by weight of the composition. The organic peroxy acid bleach precursors are defined as organic compounds that react with hydrogen peroxide in a perhydrolysis reaction to produce a peroxyacid. These bleaching aids are claimed to provide benefits including reduced hair damage at lower pH.

However, at a pH higher than 8, the present Applicant has found that these bleaching aids are more damaging to hair than usual water-soluble oxidizing agents such as hydrogen peroxide. Without being bound by theory, the Applicant believes that the conjugate base of the organic peroxyacid formed at a pH above 8 is more likely to oxidize the disulphur bonds of the keratin than other oxidizing agents such as hydrogen peroxide. The problem, however, is that hair coloration compositions, especially those with oxidative dyes, perform much poorer at lower pH, even at pH 8, than at pH 10. Finally, another difficulty is that these peroxyacid precursors are difficult to solubilize, especially in an oil-in-water emulsion, a form typical of many hair care products.

Antioxidants have also been reported to reduce hair and scalp damage [R Rajput, Understanding Hair Loss due to Air Pollution and the Approach to Management. Hair Ther Transplant 5:133. 2015; doi:10.4172/21670951.1000133 and References cited therein].

Despite these developments, there's still plenty of room for improvement in developing hair- and scalp-friendly products as evidenced by the plethora of new articles, patent submissions and products all relating to problems with hair and hair care. In this respect, there is no doubt that damage to hair caused by air pollution, various aggressive chemicals, especially the strongly aggressive chemicals, whether contained in bleaching, copper chelating, dyeing or perming compositions or in normal tap water or pool water, particularly with repeated usage or exposure, is still a huge problem. While EDTA is a good chelating agent, as noted above, it is itself damaging to hair. And, despite numerous claims, especially in the trade literature, to the contrary, our studies showed that EDDS is not an effective chelating agent for copper. Thus, there is still a need for effective treatments for hair care applications.

It is hence an object of the present invention to provide new compositions which may be a pre-treatment, treatment, or post treatment composition, capable of improved protection of human hair, particularly the structurally important keratin bonds, such as the disulphide bonds, of human hair from oxidative damage.

It is another object of the present invention to provide methods of treating hair with select compositions for reducing and/or preventing oxidative hair damage caused by UV light, blue light and air pollution.

It is another object of this invention to provide hair treatment compositions, including bleaching, dyeing, perming, restoring, shampooing and/or conditioning compositions which are less damaging to hair and/or provide protection against oxidative damage.

Furthermore, it is an object of this invention to provide such compositions which have better efficiency in terms of light shade, color evenness, color fading and hair feel than compositions without the benefit of the present invention.

It is another object of this invention to provide bleaching or dyeing compositions capable of protecting hair fibers while at the same time delivering a good lightening or dyeing effect.

It is another object of this invention to provide bleaching or dyeing compositions capable of protecting hair fibers while at the same time providing reduced scalp irritation.

SUMMARY

According to the present teachings, it has now been found that certain aryl alkanone compounds are very effective in reducing and/or inhibiting or preventing oxidative stress, or the manifestation thereof, in hair as well as in chelating iron and copper ions, ions oftentimes associated with such stress and/or other pathways to hair damage. The select aryl alkanones are found to be more effective in quenching singlet oxygen and are more stable under singlet oxygen environment than conventional antioxidants such as natural tocopherols and alpha tocopherols. Also, these aryl alkanone compounds are found to be more effective chelators than EDDS and EDTA and even better than pharmaceutical chelants such as Desferal and Deferiprone. In following, it has now been found that these compounds are very effective in protecting hair fiber from damage arising from sun light, air pollutants, oxidative treatments, shampooing and/or conditioning, and simple exposure to tap water or pool water. These compounds may be employed as a pretreatment, a post-treatment or as a component of the hair treatment composition whose other ingredients are responsible for the oxidative stress or degradation in the first place, including in shampoos and/or conditioners. In this later case, the present teachings provide many, if not most, of the desired attributes of the utopian, or nearly utopian, bleaching, dyeing or perming treatments and shampooing and/or conditioning compositions and also provide said compositions with better efficiency and efficacy in terms of their intended function, e.g., light shade, color evenness, color fading and hair feel in the case of dying and bleaching compositions.

Specifically, according to the present teachings there are provided hair treatment compositions and methods which incorporate one or more aryl alkanones according to Formula I as follows:

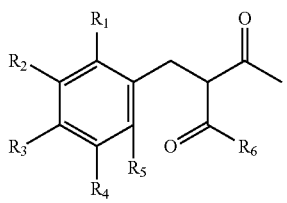

Formula I wherein $R_1$, $R_2$, $R_3$, $R_4$ and $R_5$, which may be the same or different, are each independently H, OH, alkyl or alkoxy, preferably H or a $C_1$-$C_8$, preferably $C_1$-$C_6$, most preferably a $C_1$-$C_4$, linear or branched alkyl or alkoxy group, and $R_6$ is $CH_3$ or $OR_7$ where $R_7$ is alkyl, preferably a $C_1$-$C_{12}$ alkyl.

These compounds may be incorporated into various hair care products including hair coloring products, bleaching products, perming products, shampoos, conditioners, alcoholic spray, spray gel, restorative products, hair sunscreens, and the like. Such products are well known and widely available or could be specially formulated with conventional and/or newly discovered ingredients. As an additive, these compounds render such products improved as compared to the same products without the additive, especially in terms of the prevention or reduction of oxidative-type damage to the hair.

These compounds may also be incorporated into various products or carrier compositions, especially those typical of hair care active ingredients, as a pretreatment for application prior to treatment of the hair with those products that cause oxidative damage and/or contain hair damaging ingredients. Conversely, they may be incorporated into various products or carrier compositions, as noted, as a post treatment, especially where the presence of compounds according to Formula I may interfere with the active agents of the hair care product applied/to be applied. Other post treatment products and carrier compositions incorporating compounds according to Formula I include those used/to be used by swimmers and divers and participants of other water sports whose hair is constantly affected by the chlorine and other chemicals in the pool water.

When the aryl alkanones are incorporated into the hair treatment composition itself, it is typically incorporated at a weight ratio of from 25:1 to 1:25, preferably from 15:1 to 1:15, more preferably from 10:1 to 10:1 based on the amount of the oxidizing agents in the composition. Where the composition is a pretreatment or post treatment composition which is to be applied to hair to combat oxidizing agents that are subsequently or previously applied to the hair or to which the hair is exposed, the amount of the aryl alkanones is generally from about 0.1 to 15, preferably from about 0.5 to 10, more preferably from about 1 to about 4, most preferably from about 1.2 to 3 percent by weight of the pre- or post-treatment composition. Of course, lesser or greater amounts than recited above may also be used so long as the objective of the present teaching is attained without adversely affecting the hair or the treatment applied to the hair. In this respect, the present teaching and the appended claims pertain to any effective amount.

The application of the treatment composition containing the aryl alkanones is consistent with the instructions of the composition for its intended purpose. In the case of pre-treatments and post-treatments the composition may be applied prior to or subsequent to, respectively, the application of an oxidative hair treatment composition or following exposure of the hair to an oxidizing condition, namely sun exposure, air pollutants, etc. In the case of post treatments, while it may be preferred to rinse the post treatment composition out of the hair following application and allowing it to stand in the hair for a few minutes or so, one can also leave it in the hair. For example, it may be desirable to apply the post-treatment composition following a swimming session or after showering following swimming to provide additional protection. Conversely, applying it to the hair without rinsing prior to swimming will also protect the hair while swimming. For daily protection of normal or dyed or bleached hair, the present inventive compositions can be applied on to and/or worked into the hair as an alcoholic spray, spray gel, spray foam, leave-on-conditioner, hair restorative treatment, etc. Additionally, the compositions according to the present teaching optionally contain one or more broad-spectrum sunscreens for providing extra protection against sun and pollution-induced hair damage.

DETAILED DESCRIPTION

For convenience, given the multiple applications of the aryl alkanones in hair care compositions and methods, the present invention will be discussed in terms of its use in a hair coloring composition. The invention is not, however, limited thereto as set forth in the Summary and below.

As used herein and in the appended claims the term "oxidative hair coloring composition" refers to custom formulated and ready-to-use compositions which can change the color of hair and which typically comprise an alkalizing agent, an oxidizing agent and one or more oxidative primary dyes. A "two-component" oxidative hair coloring composition means an oxidative hair coloring composition which is obtained by mixing a tint component and an oxidizing component shortly before or at the time of application of the composition to hair. The tint component generally comprises the oxidative primary dyes and the alkalizing agent whereas the oxidizing component comprises the oxidizing agent. A "Dye Pretreatment" refers to a composition that is applied to the hair prior to treatment with an oxidative hair coloring composition. The term "component" means an individual compound, ingredient or mixture of compounds or ingredients which is mixed by the user or formulator with one or more other components for preparing the hair care composition, especially the ready-to-use oxidative hair coloring composition to be applied to the hair. The term "user" when used in the context of hair coloring means the person preparing the hair coloring composition for application to the hair, whether formulating the coloring composition from a plurality of components or preparing the composition for application from a premade coloring composition. This person may be a professional hair stylist working in a salon, an assistant who prepares the hair coloring composition for the stylist, a person who is applying the hair coloring composition to their own hair or someone doing the same or helping them in doing so.

Additionally, as used herein the term "lift" refers to the amount by which or the extent to which the natural hair pigment is removed by the coloring composition. The amount of lift provided by different hair coloring compositions can be compared using a natural dark human hair sample and measuring the change of color achieved following application of the compositions. The change in color can be measured using well known parameters such as L*a*b* values. A composition can be said to provide a higher lift than another composition when the ΔL* value measured for a given treated sample of dark hair is higher for that one composition than for another composition, using the same experimental conditions. The denomination Level 2 (herein used interchangeably with "demi-permanent" or "tone-on-tone") and Level 3 (herein used interchangeably with "permanent") are commonly used in the hair care trade to differentiate compositions with medium and high lift, respectively.

As used herein and the appended claims the term "hair coloring oxidizing agent" refers to an electron accepting compound or a combination of electron accepting compounds suitable for use in hair coloring compositions for removing the natural color of hair (e.g., by destroying the melanin pigment) and reacting with oxidative primary dyes to provide an oxidative hair color. The most commonly used oxidizing agent in the art is hydrogen peroxide. Similarly, a "hair coloring alkalizing agent" refers to compounds or a combination of compounds suitable for raising the pH to alkaline level in hair coloring compositions, in particular to a pH between 9 and 11. Unless otherwise indicated, all percentages are by weight based on the weight of the oxidative hair coloring composition or, as context allows, the composition being discussed, as applied to the head or hair. For example, in the case of the ready-to-use coloring composition, the weights are based on the composition as applied to the hair after the two or more components have been mixed. In the case of concentrates, the percentages are based on the total weight of the concentrate. Similarly, all ratios are weight ratios unless specifically stated otherwise.

Finally, throughout this specification Applicant refers to the fact that something, most notably the presently described compositions, "may be used" for a given purpose or that the certain components or ingredients "may be" used or incorporated into a formulation. It is to be understood that Applicant's use of the phrase "may be" is not to be construed as meaning it is a theoretical possibility, but that it is or is an option. Accordingly, the phrase "may be" is to be construed as "can be." The same is true for Applicant's use of the term "could" in terms of what one could do. This language is intended to present an option that one can follow, not a mere theoretical possibility of what one could try.

According to the present teachings it has now been found that the incorporation of certain aryl alkanones into hair treatment, pretreatment and/or post treatment compositions provide a number of benefits to the hair, especially benefits in the nature of reduced hair damage and/or the prevention of hair damage, color fading resulting from oxidative conditions, especially from the use of hair treatments containing oxidizing agents, most especially dyes and other hair coloring compositions, or exposure to sun or air pollutants. Such benefits have been found with hair treatment, pretreatment and post treatment compositions and the use thereof which incorporate one or more aryl alkanones according to the Formula I as follows:

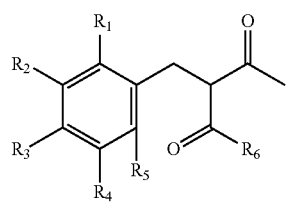

Formula I wherein $R_1$, $R_2$, $R_3$, $R_4$ and $R_5$, which may be the same or different, are each independently H, OH, alkyl or alkoxy, preferably H or a $C_1$-$C_8$, preferably $C_1$-$C_6$, most preferably a $C_1$-$C_4$, linear or branched alkyl or alkoxy group and $R_6$ is $CH_3$ or $OR_7$ where $R_7$ is alkyl, preferably $C_1$-$C_{12}$ alkyl, alone or in combination with one or more broad-spectrum sunscreens.

Preferred compounds according to Formula I are those in which
$R_1$=$R_5$=H and each of $R_2$, $R_3$, and $R_4$ is independently a $C_1$-$C_4$ linear or branched alkoxy or $C_1$-$C_8$ linear or branched alkyl and $R_6$ is $CH_3$ or $OC_2H_5$ or in which
$R_1$=$R_2$=$R_5$=H; and each of $R_3$ and $R_4$ is independently a $C_1$-$C_4$ linear or branched alkoxy or $C_1$-$C_8$ linear or branched alkyl; $R_6$ is $CH_3$ or $OC_2H_5$.

Especially preferred compounds of Formula I are as follows:
Compound 1A: $R_1$=$R_3$=$R_5$=OMe and $R_2$=$R_4$=H; $R_6$=$CH_3$
Compound 1B: $R_1$=$R_3$=$R_5$=H and $R_2$=$R_4$=OMe; $R_6$=$CH_3$
Compound 1C: $R_1$=$R_2$=$R_5$=H and $R_3$=$R_4$=Me; $R_6$=$CH_3$
Compound 1D: $R_1$=$R_2$=$R_5$=H and $R_3$=$R_4$=OMe; $R_6$=$CH_3$
Compound 1E: $R_1$=$R_2$=$R_4$=$R_5$=H; $R_3$=OMe; $R_6$=$CH_3$
Compound 1F: $R_1$=$R_5$=H; $R_2$=$R_3$=$R_4$=OMe; $R_6$=$CH_3$
Compound 1G: $R_1$=$R_5$=H; $R_2$=$R_3$=$R_4$=Me; $R_6$=$CH_3$
Compound 1H: $R_1$=$R_4$=OMe; $R_2$=$R_3$=$R_5$=H; $R_6$=$CH_3$
Compound 1I: $R_1$=$R_3$=$R_5$=H; $R_2$=$R_4$=Me; $R_6$=$CH_3$
Compound 1J: $R_1$=$R_2$=$R_4$=$R_5$=H; $R_3$=Me; $R_6$=$CH_3$
Compound 1K: $R_1$=$R_3$=$R_4$=$R_5$=H; $R_2$=Me; $R_6$=$CH_3$
Compound 1L: $R_1$=$R_3$=$R_4$=$R_5$=H; $R_2$=OMe; $R_6$=$CH_3$
Compound 1M: $R_1$=$R_2$=$R_5$=H; $R_3$=OH; $R_4$=$OCH_3$; $R_6$=$CH_3$
Compound 1N: $R_1$=$R_3$=$R_5$=H; $R_2$=$R_4$=Me; $R_6$=$CH_3$
Compound 1P: $R_1$=$R_2$=$R_4$=$R_5$=H; $R_3$=Me; $R_6$=$CH_3$
Compound 1Q: $R_1$=$R_2$=$R_4$=$R_5$=H; $R_3$=OMe; $R_6$=$CH_3$
Compound 2A: $R_1$=$R_3$=$R_5$=OMe and $R_2$=$R_4$=H; $R_6$=$OC_2H_5$
Compound 2B: $R_1$=$R_3$=$R_5$=H and $R_2$=$R_4$=OMe; $R_6$=$OC_2H_5$
Compound 2C: $R_1$=$R_2$=$R_5$=H and $R_3$=$R_4$=Me; $R_6$=$OC_2H_5$
Compound 2D: $R_1$=$R_2$=$R_5$=H and $R_3$=$R_4$=OMe; $R_6$=$OC_2H_5$
Compound 2E: $R_1$=$R_3$=$R_5$=H; $R_2$=$R_4$=Me; $R_6$=$OC_2H_5$
Compound 2F: $R_1$=$R_5$=H; $R_2$=$R_3$=$R_4$=OMe; $R_6$=$OC_2H_5$
Compound 2G: $R_1$=$R_5$=H; $R_2$=$R_3$=$R_4$=Me; $R_6$=$OC_2H_5$
Compound 2H: $R_1$=$R_4$=OMe; $R_2$=$R_3$=$R_5$=H; $R_6$=$OC_2H_5$
Compound 2I: $R_1$=$R_2$=$R_4$=$R_5$=H; $R_3$=Me; $R_6$=$OC_2H_5$
Compound 2J: $R_1$=$R_2$=$R_4$=$R_5$=H; $R_3$=OMe; $R_6$=$OC_2H_5$ Compound 2K: $R_1=R_3=R_4=R_5=H$; $R_2=Me$; $R_6=OC_2H_5$ Compound 2L: $R_1=R_3=R_4=R_5=H$; $R_2=OMe$; $R_6=OC_2H_5$ Compound 2M: $R_1=R_2=R_5=H$; $R_3=OH$; $R_4=OCH_3$; $R_6=OC_2H_5$ The aryl alkanones employed in the present invention typically exist as keto-enol tautomers in aqueous solvents or aqueous based compositions. Exemplifying this phenomenon, the keto-enol tautomers of Compound 1D are shown below in Formula II. Though the ratio of enol to keto for the aryl alkanones when present as tautomers may vary widely, the tautomer mixture is typically from about 40% to 99%, preferably from about 60% to 98%, keto. Accordingly, the present invention pertains the use of both the aryl alkanone as the ketone as well as the mixture of the keto-enol tautomers, i.e. one may start with the solid aryl ketone which is then formulated into an aqueous or aqueous based carrier, diluent or composition such that the aryl alkanone when formulated in the hair care product or component thereof or as applied to the hair is in the tautomer form.

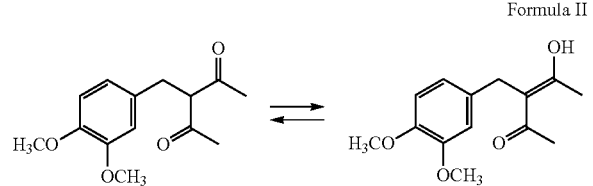 [SMILES: COc1ccc(CC(C(C)=O)C(C)=O)cc1OC ; COc1ccc(C/C(C(C)=O)=C(/C)O)cc1OC]

Formula II

While not intending to be bound by theory, it is believed that the efficacy of the aryl alkanone compounds arises, at least in part, from a chelating action of these compounds, a property which is believed to be associated with, directly or indirectly, the presence of the two acetyl groups or one acetyl and one ester group at the C-3 position of the aryl alkanone compounds. Another surprising property found with these aryl alkanones is a quenching property. Specifically, these compounds act as quenchers suppressing free radicals from being formed at the source and relaxing the excited state back to the ground state before they can form free radicals. Surprisingly, these compounds are also found to be non-sacrificing molecules. This contrasts with conventional antioxidants which work by scavenging singlet oxygen and are sacrificing molecule (Wondrak G, Photochem Photobiol Sci, Endogenous UVA-photosensitizers: mediators of skin photodamage and novel targets for skin photoprotection, 5:215-237, 2006).

As noted above, given the many applications for the aryl alkanone compounds in hair care applications, this discussion will focus on hair coloring compositions, most especially the present invention will be described in terms oxidative hair coloring compositions which, again as noted above, generally comprise an alkalizing agent, an oxidizing agent and oxidative primary dyes. While the aryl alkanones have broad application and utility, as noted, it is preferred that the aryl alkanones be free of hydroxy substitution, particularly on the aromatic ring, in the case their use in hair coloring agents: indeed the presence of phenolic OH on the aryl alkanone is discouraged for use in hair coloring compositions and treatments.

Although the most commonly used alkalizing agent in the art is ammonia or other ammonia based or ammonia precursor agents, "non-ammonia" alkalizing agent are also employed and, in particular, are contemplated by the present teachings. Indeed, according to the preferred embodiment of the oxidative hair coloring compositions of the present invention, the oxidative hair coloring compositions comprise at least one non-ammonia alkalizing agent. Such non-ammonia alkalizing agents include, especially the alkanolamines including monoethanolamine (MEA), diethanolamine, triethanolamine, monopropanolamine, dipropanolamine, tripropanolamine, 2-amino-2-methyl-1,3-propanediol, 2-amino-2-methyl-1-propanol (a.k.a. aminomethylpropanol, AMP), 2-amino-2-hydroxymethyl-1,3-propanediol and mixtures or combinations of any two or more of the foregoing.

Monoethanolamine (MEA) or aminomethylpropanol (AMP) are commonly used in ammonia-free hair dye products and are among the, if not the, preferred non-ammonia alkalizing agents. They may be used alone or in combination with each other or one or more other alkalizing agents, including ammonia or ammonia-based agents; but are preferably used alone or in combination with one or more other non-ammonia alkalizing agents. Especially preferred is monoethanolamine, alone or in combination with one or more other non-ammonia alkalizing agents.

The amount of the non-ammonia alkalizing agent is that which is conventional in hair coloring compositions. Generally, the amount is from about 1 to about 10%, preferably from about 1 to 5% by weight of the oxidative hair coloring composition.

It is also contemplated that the compositions according to the present teachings may include one or more alkalizing agents which are not non-ammonia alkalizing agents. However, if present, they are present at relatively low levels, for example less than 0.5% by weight. Most preferably the compositions according to the present teachings are substantially free of ammonia: i.e., are free of ammonia or only contain trace or negligible quantities thereof, especially quantities that would otherwise provide an alkalizing effect.

The second component of the oxidative hair coloring compositions according to the present teachings is the oxidizing component which typically comprises or includes one or more oxidizing agents. Suitable oxidizing components include any usual oxidizing composition known in the art for this purpose. In particular, the oxidizing component may be an oil-in-water emulsion of hydrogen peroxide ($H_2O_2$). The oxidizing agent may be more generally selected from hydrogen peroxide, sodium periodate, urea peroxide, melamine peroxide, perborates, percarbonates, perphosphates, persilicates, persulphates, peroxidises and mixtures thereof.

Where the hair coloring composition is a two-component oxidative hair coloring composition whose first component includes an oxidizing agent in with the tint and a second component which includes an oxidizing agent, the oxidizing agent in the first component may be the same as or different from that in the second component and is preferably, in both cases, hydrogen peroxide. The concentration of the oxidizing agent may be the same or different in the first and second components; however, it is preferred that a higher concentration of the oxidizing agent is used in the second component in order to maintain a certain concentration when the oxidative hair coloring composition is on the head. Of course, the selection of oxidizing agents may also affect the relative concentrations of the oxidizing agents in the two components. Typically, in a standard, non-ammonia based, two-component oxidative hair coloring composition, especially where the oxidizing agent is hydrogen peroxide, the concentration of the oxidizing agent ranges from 1% to 3% by weight of the composition. For example, a commercially available hair coloring product will usually be mixed in 1:2 ratio (by weight) with a 4% or 1.9% $H_2O_2$ emulsion, thus resulting in a 2.7% $H_2O_2$, and 1.3% concentration on-head.

The third component is the dye component which, particularly in the case of permanent hair coloring compositions, comprises several elements, most especially primary intermediates and coupling agents which react in the presence of the oxidizing agent to produce the actual dye molecules; though it is also understood that the primary intermediates may couple to themselves to form dye molecules. The primary intermediates are typically para-diamine and para-amino phenols, especially 1,4-diaminobenzene, para-aminophenol, and 2,5-diamino phenol. The intermediates are oxidized by the oxidizing agent, especially hydrogen peroxide, to produce reactive species which then react with the coupling agents to produce the dyes. The coupling agents, also known as color couplers, are well known and react with the primary intermediates in the presence of the oxidizing agent to produce the dye. Exemplary coupling agents include resorcinol, m-aminophenol, 2-methyl-5-aminophenol, p-phenylenediamine, 2,4-diaminoanisole, 1,5-dihydroxynephthalene, 4-methoxy-3-aminophenol, 2,4-diaminophenoxyethanol, m-diethylaminophenol and p-amino-o-cresol. Oftentimes multiple coupling agents will be used in a given hair color composition. Such components are employed in conventional amounts well known in the industry.

Of course the oxidative hair coloring compositions may comprise additional components or additional components may be applied to the hair during the treatment process. These additional components may include an oxidizing agent or be free of oxidizing agents. When a third component is employed in a hair coloring process, particularly when it is applied after application of the two-component product, it is preferable that the concentration of the oxidizing agent in the second component be greater than that in the first component, irrespective of whether they are the same or different oxidizing agents. This is especially desirable where the third component is free of oxidizing agents or has a low concentration thereof since its application to the head will result in a dilution of the oxidizing agents contributed by the other components, especially the first and second components. Overall, it is preferred that the concentration of the oxidizing agent, especially if it is $H_2O_2$, in the first component of the oxidative coloring composition, especially one containing a third component, be, for example, from 1% to 6%, in certain embodiments from 2% to 4%, in particular from 2.5 to 3.5% of the first component. Using too high a concentration of hydrogen peroxide or other oxidizing agent may not provide the desired level of lift or minimize or negate the additional lift provided by the compositions of the present invention, while being damaging for the hair fiber. The second oxidizing agent, which again may be the same or a different oxidizing agent than the first, though it is preferably hydrogen peroxide, will be present at the same or, preferably, a slightly higher concentration, for example, from 3 to 10% by weight of the second component, in particular from 6 to 9%.

Notwithstanding the foregoing recitation of ranges for the alkalizing agent and the oxidizing agents, it is to be appreciated that the two are typically employed in relative proportions to one another. Generally, the amount of alkalizing agent to oxidizing agent is from about 0.8:1 to 2:1, preferably from about 0.9:1 to 1.6:1, most preferably from about 1:1 to 1.2:1. However, when the third component mentioned above is used, the weight ratio of alkalizing agent to oxidizing agent (in particular a ratio of non-ammonia alkalizing agent, especially MEA:$H_2O_2$) will be somewhat higher, generally from 1:1 to 4:1, preferably from about 1.1:1 to 3:1, as this was found to provide a good balance between high lift and an acceptable level of oxidative hair damage.

The hair treatment and pre- and post-treatment compositions of the present teachings may, and typically do, include one or more additional ingredient for varying purposes, some of which pertain to the stability of the compositions, others for improved performance thereof, and others still for improving the look, feel and/or smell thereof. Exemplary additional ingredients include radical scavengers, sunscreen actives, solubility enhancers, thickeners, and the like, as described in more detail below.

A preferred, though not required, additional ingredient of the compositions according to the present teaching is one or more radical scavengers. Radical scavengers are materials, which may be individual compounds, polymers, or the like, which can react with a carbonate radical to convert the carbonate radical to a less reactive species. Exemplary radical scavengers include alkanolamines, amino sugars, amino acids, esters of amino acids and mixtures thereof. For example, the following compounds can be employed as radical scavengers: ethylamine, monoethanolamine, 2-methoxyethylamine, 3-amino-1-propanol, 4-amino-1-butanol, 5-amino-1-pentanol, 1-amino-2-propanol, 1-amino-2-butanol, 1-amino-2-pentanol, 1-amino-3-pentanol, 1-amino 4-pentanol, 3-amino-2-methylpropan-1-ol, 1-amino-2-methylpropan-2-ol, 3-aminopropane-1,2-diol, glucosamine, N-acetylglucosamine, glycine, arginine, lysine, proline, glutamine, histidine, sarcosine, serine, glutamic acid, tryptophan, morpholine, piperidine, and mixtures thereof, and the salts such as the potassium, sodium and ammonium salts thereof and mixtures thereof.

Radical scavengers are typically employed in an amount from about 0.1% to about 10%, preferably from about 1% to about 7% by weight, depending upon the hair treatment or pre- or post-treatment composition in which it is employed as well as the selection of the radical scavenger or combination of radical scavengers. When the carbonate ion is present in the hair care composition, the radical scavenger is typically present in an amount such that the weight ratio of radical scavenger to carbonate ion is from 2:1 to 1:4. Although not required, given the overlap between the alkalizing agent and the radical scavengers, it is preferred that radical scavenger is not the same as, and more preferably is not of the same species as, the alkalizing agent.

Although the discussion has focused on compounds and species that act as radical scavengers, it is also to be appreciated that the radical scavenger can be formed in situ in the hair treatment or hair pre- or post-treatment compositions prior to application to the hair fibers. In this case, a pre-cursor for the radical scavenger is incorporated into the formulation of the composition and the same includes ingredients and/or is exposed to conditions which convert the precursor to a radical scavenger.

Generally speaking, the hair care compositions of the present teaching comprise water as the preferred and principal solvent, carrier or diluent; though it is to be appreciated that the water or additional water may be added to the compositions at the time of application. In this latter respect, the compositions may be prepared and/or sold as concentrates which are then diluted in water or a water-based diluent or carrier either at the time of use or at the time of packaging for commercial/consumer distribution. Most typically, the compositions are employed as water-based or water-in-oil based emulsions or suspensions.

Inasmuch as certain, if not many, of the ingredients employed in the present hair care compositions have poor, low or slow solubility in water, it is desirable to employ solubility enhancers to increase solubility and/or the speed of solubilization. The two preferred classes of solubility enhancers are organic solvents and surfactant systems. The solubility enhancers are especially useful when incorporating a precursor composition or concentrate into water or a water-based solution: the precursor composition containing, e.g., all or most of the key or active components of the hair care composition for its intended purpose.

Preferred organic solvents are those that are miscible with water and innocuous to the skin. Organic solvents suitable for use herein include $C_1$-$C_{10}$ mono- or polyhydric alcohols and their ethers as well as mixtures and reaction products of glycerin with monohydric and dihydric alcohols and their ethers. Preferred organic solvents are or include alcoholic residues containing 2 to 6 carbon atoms. A particularly preferred group of organic solvents includes ethanol, isopropanol, n-propanol, butanol, octyldodecanol, phenyl ethyl benzoate, propylene glycol, ethylene glycol monoethyl ether, hexylene glycol, dimethyl isosorbide, PEG-300, PEG-400, PEG-400/water (1:1) and mixtures thereof.

The organic solvents, which may be and preferably are present in or added to the concentrate prior to the addition of or to water or a water-based diluent or carrier, are typically employed at a level of from about 0.1 to 20 wt %, preferably from about 0.1 wt % to about 15 wt %, and most preferably from about 0.5 wt % to about 10 wt %, based on the total weight of the concentrate or the ingredients to be added to the water or water-based diluent.

The second class of solubility enhancers useful in the present invention is the surfactants. Surfactants, especially for hair care compositions, are well known and readily available. A particularly suitable class of surfactants is the cationic surfactants. One type of preferred cationic surfactant is amine based cationic surfactants and includes alkyl amines, alkylethoxy amines, ethoxylated alkyl amines and alkyl alkanol amities wherein the preferred alkyl groups have 1 to about 22 carbon atoms. Additionally, the specific surfactant type and/or species can have a mixture of chain lengths, e.g., methyl and hexadecyl, or if different species or types are used, each can have the same or a different chain length. As used herein the term "amines" is to be understood as including primary, secondary, tertiary and quaternary amines.

A second type of preferred cationic surfactant is amido-amines and includes $C_{12}$-$C_{22}$ alkyl- or alkylethoxy-mono, di and higher (poly)amidoamines, which can be ethoxylated or unethoxylated. Examples include sodium dimethylaminopropyl coco-aspartamide, cocoamidopropyl dimethylamine, olivamidopropyl dimethylamine, soyamidopropyl dimethylamine, tallowamidopropyl dimethylamine, stearamidoethyl dimethylamine and mixtures thereof.

Another preferred class of surfactant suitable for use as a solubility enhancer is the nonionic surfactants. This class includes long chain fatty alcohols; mono, di and triglycerides and their derivatives; long chain ($C_{12}$-$C_{18}$) alcohol ethoxylates; and mixtures thereof. Examples include: steareth 20, oleth 10, laureth 4, PEG-400, PEG-12 glyceryl dioleate, glycerol stearate, sorbitan oleate, PPG-9 buteth-12 etc. and mixtures thereof.

The level of surfactants used as solubility enhancers, particularly in the dye precursor mixture, can generally range from 0.1 wt % to about 30 wt %, preferably from about 0.2 wt % to about 20 wt %, and most preferably from about 0.25 wt % to about 15 wt %, based on the total weight of the concentrate or the ingredients to be added to the water or water-based diluent.

Both solvents and surfactants (as well as combinations of solvents and/or combinations of surfactants) can and often are combined to achieve the desired state of solubility of the ingredients, especially the primary intermediate and coupler in the dye concentrate. However, it has been found that the type and level of solubility enhancer affect the ability of the oxidative dyes to absorb into the hair fibers and be retained after development. Although this can be difficult to predict, the optimum type and level of solubility enhancer can be determined empirically by treating a standard hair sample under controlled conditions with a concentrate mixture or the tint or dye precursor composition and developing the color with an oxidizing agent.

Another optional, though preferred, ingredient in the hair care compositions of the present teachings is a thickener or mixture of thickeners for enhancing the viscosity of the hair care compositions and/or their components. Hair care compositions in the nature hair coloring compositions will generally employ one or more thickeners in the oxidation hair colorant composition (aka the first component) and/or in the developer compositions (aka the second component and/or the third component) as well as in the concentrates and/or precursor part of each. Suitable thickeners include natural and synthetic, long chain fatty alcohols having from about 11 to about 22 carbon atoms, preferably 11 to 18 carbon atoms, in the long fatty chain.

Exemplary thickeners include lauryl alcohol, oleyl alcohol, myristyl alcohol, stearyl alcohol, behenyl alcohol and the like, and mixtures thereof. Several suitable mixtures are available commercially and are exemplified by the material containing a mixture of synthetic alcohols with 12 to 15 carbons in the alkyl chain sold under the trademark NEODOL 25 by Shell Chemical Company, and the material containing a mixture of synthetic alcohols with chain lengths of 12 to 16 carbons sold under the trademark ALFOL 1216 Alcohol by Conoco Chemicals. As noted, the fatty alcohols can be used alone or as a combination of two or more such alcohols. When included in the compositions of the present teachings, alcohol based/alcohol functionality containing, thickeners are preferably present in an amount of from about 0.5 to about 10 weight percent of the composition, more preferably from about 2 to about 8 weight percent.

As noted, the suitable fatty alcohols include their ethoxylated species as well. Preferred ethoxylated fatty alcohols are those wherein an average of one or two moles of ethylene oxide moieties or units are present in the fatty alcohol per mole of fatty alcohol. These can be used in place of the fatty alcohols themselves. Examples of such useful ethoxylated fatty acids include ethylene glycol cetyl ether, polyoxyethylene (2) stearyl ether, and the like; the exemplary compounds having CTFA Dictionary names of Ceteth-1 and Steareth-2, respectively.

Thickening agents suitable for use in the compositions of the present teaching may also be selected from oleic acid, cetyl alcohol, oleyl alcohol, sodium chloride, cetearyl alcohol, stearyl alcohol, synthetic thickeners such as CARBOPOL, ACULYN® 28, STRUCTURE 2001, 3001, and XL, and ACROSYL® and mixtures thereof. Preferred thickeners for use herein are ACULYN® 22, steareth-20 methacrylate copolymer; ACULYN® 44 polyurethane resin and ACUSOL® 830, acrylates copolymer that are available from Rohm and Haas, Philadelphia, Pa., USA. Additional thickening agents suitable for use herein include sodium alginate or gum arabic, or cellulose derivatives, such as methylcellulose or the sodium salt of carboxymethylcellulose or acrylic polymers. Such additional thickeners are used in conventional amounts and/or as directed by their suppliers. In any event, they are used in an amount sufficient to attain the desired viscosity of the product which can be found by simple trial and error, particularly if one starts with the foregoing guidelines.

In addition to the aforementioned optional, though preferred, ingredients, the hair care compositions of the present teaching may and preferably do contain a wide range of additional optional ingredients. For example, the compositions may comprise one or more mildness enhancers (such as cholesterol and its derivatives), hair swelling agents, anticaking agents, antioxidants, binders, biological additives, bulking agents, chelating agents, colorants, cosmetic astringents, cosmetic biocides, sunscreens, denaturants, drug astringents, emulsifiers, film formers, fragrance components, humectants, opacifying agents, plasticizers, preservatives, propellants, reducing agents, foam boosters, hydrotropes, suspending agents, detanglers, ultraviolet light absorbers, photostabilizers and viscosity increasing agents, hair fiber lubricants, sequestrating agents, amino acids, ingredients that impact hair shine, hydrolyzed proteins, etc. as well as combinations of any two or more of the foregoing. Such ingredients are employed in conventional amounts consistent with the art for their respective type of hair care composition.

For example, it may desirable and advantageous, especially from a consumer appeal perspective, to include agents that condition the hair to improve the ease of combing or brushing, (e.g. detanglers) and impart a silky/moisturized feel to the hair after it dries. Such agents include fatty long chain amines and their derivatives, silicones such as dimethicone and amodimethicone, long chain fatty alcohols and mixtures of these materials.

As noted above and at the outset, the aryl alkanones, or mixtures of two or more of such compounds, can be incorporated into existing hair care products, including hair treatments, pre-treatments and post-treatment products. Exemplary products include, but are not limited to, bleaching, dyeing or perming treatments, hair restorative products, and shampooing and/or conditioning compositions. In the case of those products comprising a plurality of components, e.g., hair coloring systems, which may be applied concurrently or sequentially, they may be incorporated into some or all of the individual components or parts. Similarly, in the case of products sold as kits containing multiple products, e.g., a kit containing shampoo and a condition, these compounds may be in some or all of the products making up the kit.

Of course, it is also to be appreciated that treatment and pre- and post-treatment compositions comprising the aryl alkanone compounds may comprise the aryl alkanone as the sole or key active ingredient or may be combined with one or more of the aforementioned optional or additional optional ingredients. For example, if it were to be found that the aryl alkanone interfered with or interacted with the coloring agent or its ability to bind to or color the hair; one could apply a rinse solution of the aryl alkanone following completion or near completion of the hair coloring process. Similarly, one could make a product which is intended to be applied to the hair prior to and/or subsequent to swimming to prevent and/or reduce the oxidative effect of the chlorine in the pool water, especially that which remains in the hair even following showering. In both of these respects, such formulations could be prepared by dissolving or solubilizing the aryl alkanone in a suitable solvent or carrier which is suitable or known for use in application to the hair. To aid in their preparation, it is also desirable to solubilize the aryl alkanone(s) in a solvent or emollient like propane diol, propylene glycol or isosorbide dicaprylate and then add this to a suitable carrier or like delivery system. This same technique may also be used for preparing or aiding the preparation of the aryl alkanone for adding to the coloring agent right before applying to the hair, to the conditioner or other hair care product into which it is to be incorporated.

The methodology for application of the hair care compositions comprising the aryl alkanone to the hair is or should be consistent, with the methodology for the application or use of the product into which it is incorporated. Where the aryl alkanone is the key active ingredient and used as the treatment itself, it is typically employed in the same manner as one would use a conventional hair conditioner or hair spray. For example, if employed as a pre-treatment or a post-treatment a small amount, perhaps a teaspoon quantity or so, is applied to the palm of one's hand and worked into wet hair.

It is understood that the methods of use described herein are for illustrative purposes only and that various modifications or changes in light thereof will be suggested or apparent to one of ordinary skill in the art without departing from the scope of the present invention. For example, application of a hair coloring composition according to the present teachings to the hair may be undertaken in several ways. In one method, the hair coloring composition may be applied to the whole of the strands of the hair, i.e., from the root of the hair to the tip of the hair. Alternatively, one may apply the hair coloring composition only to the root portion of the hair, generally that portion of the hair strands which is between the scalp and 2.5 cm from the scalp or less, more typically about 1 cm or less, especially 0.5 cm or less, depending on the application method, tool, and accuracy. Another option is to apply the hair coloring composition to a portion of the hair from a point intermediate the scalp and the ends and ending at the ends. In each instance, whether whole strand application, root application or ends application, the coloring agent may be applied to the entire head or only to a portion thereof, as desired. Application of a hair coloring composition to a portion of hair is commonly referred to as high-lighting or low-lighting. In this instance, a portion of hair is physically separated from the whole head of hair in a hair bundle through the use of a number of devices including a plastic cap through which the hair bundles are formed when hair is pulled through orifices in the plastic cap, metal foils encompassing a hair bundle, strand separators applied to hair at the root portion, or similar devices.

In hair coloring procedures, it is also common, though optional, to employ a hair conditioning agent which is most often provided in a separate container. In this instance, the conditioner can be mixed immediately before use and applied together with the other components of the hair coloring composition or it may be applied as a post-treatment immediately after application of the hair coloring composition or after rinsing the hair coloring composition from the hair.

According to one method for oxidatively coloring hair, the method comprises (a) mixing a tint component, an oxidizing component, and, optionally, a third component comprising a second non-ammonia alkalizing agent together to form a hair coloring composition, (b) applying the hair coloring composition to the hair to form a treated hair surface, (c) allowing the hair coloring composition to remain in the hair for a period of 15-60 minutes, preferably, 20-30 minutes, depending upon the specific hair coloring composition, and then (d) removing the hair coloring composition from the treated hair surface. Optionally, one may also work the hair coloring composition into the treated hair surface by hand or by a tool for a few minutes after application to ensure uniform application to the entire treated hair surface. Again, the hair coloring composition is then allowed to remain in the treated hair while the final hair color develops. Thereafter the hair is then rinsed thoroughly with tap water and allowed to dry. In this instance, the hair coloring composition will further comprise the aryl alkanone or the hair will have been pre-treated with a pretreatment composition comprising the same and/or will be treated with a composition comprising the aryl alkanone concurrent with or subsequent to the application the hair coloring composition, e.g., before or after the aforementioned rinse step. If applied after the rinse step, the post-treatment composition is allowed to stand in the hair for a few minutes, generally 10 or less, and then rinsed out of the hair.

Similarly, in the case of a hair conditioning composition, an appropriate amount of the hair fiber conditioning composition containing the aryl alkanone is applied to wet hair and worked into the hair for a few minutes (to insure uniform application to all of the hair). The composition is then allowed to remain on the hair for a time period of less than about 20 minutes, preferably less than about 15 minutes, more preferably from about 10 seconds to about 10 minutes. The conditioner is then thoroughly rinsed from the hair with water and dried.

In yet another embodiment of the present invention the oxidative hair coloring systems or bleaching compositions may comprise as an optional fourth component a color refresher composition. These color refresher compositions comprise at least one pre-formed dye and, optionally, though preferably, one or more of the above-mentioned aryl alkanone compounds. The color refresher compositions are typically applied to the hair immediately or shortly after the primary oxidative color treatment, generally from about 1 minute to about 30 minutes following the color treatment; though they can also be applied any time following the color treatment up to about 60 days after color treatment. Such color refresher compositions can be used to increase the initial color obtained and or boost the color during the wash and style cycle until the next oxidative coloring or bleaching event. Alternatively, the color refresher composition may be comprised within the fiber or hair fiber conditioning composition thereby ensuring a color boost with each application of the fiber or hair fiber conditioner treatment.

In yet another embodiment of the present invention the hair spray systems or conditioner compositions for protecting hair from damage caused by sun exposure and/or air pollutant may comprise sunscreens as an optional component of the composition. Sunscreen compositions are commonly used during outdoor work or leisure as a means for providing protection of exposed skin/scalp/hair against acute and chronic adverse effects of solar radiation such as sunburn, cancer and photo-aging, hair damage, color fading. Many effective sunscreen preparations are sold commercially and/or are described in the cosmetic and pharmaceutical literature. In general sunscreen preparations are formulated as creams, lotions, spray or oils containing, as the active agent, an ultra violet radiation absorbing or blocking compound. The sunscreen functions by absorbing or blocking ultra-violet radiation, preventing its penetration into the skin, scalp and hair. The ability of sunscreen to protect against the generation of reactive oxygen species (ROS) within the skin or scalp has not been identified. Although sunscreens do prevent erythema and are recommended to be used as part of safe-sun practices, current research suggests that photoprotection is also needed to reduce ROS levels within the skin (K M Hanson and R T Clegg, Bioconvertible vitamin antioxidants improve sunscreen photoprotection against UV-induced reactive oxygen species, J Cosmet Sci, 54:589-598, 2003).

Organic sunscreens are classified into UV-A filters, UV-B filters or broad-spectrum filters (UV-A and UV-B functionality in a single molecule) depending on the type of radiation they absorb. UV-A sunscreens absorb radiation in the 320 to 400 nm regions of the ultra violet spectrum and UV-B sunscreens absorb radiation in the 290 to 320 nm regions of the ultra violet spectrum (See Sunscreens, Regulations and Commercial Development, Third Edition, Nadim A. Shaath, Ed., Taylor & Francis, 2005). Broad-spectrum sunscreens (UV-A and UV-B functionality) absorb radiation in the 290 to 400 nm region of the ultra violet spectrum and have two maximums, one in the UV-B region and the other in the UV-A region. Representative references relating to UV sunscreens include Gonzalez et. al. —U.S. Pat. No. 7,186,404; Aust et. al. —U.S. Pat. No. 7,175,834; Roseaver et al. —U.S. Pat. No. 7,172,754; Simoulidis et al. —U.S. Pat. No. 7,175,835; Mongiat et. al. —U.S. Pat. No. 7,101,536; Maniscalco—U.S. Pat. No. 7,078,022; Chaudhuri et. al. —U.S. Pat. No. 6,165,450; Forestier et. al. U.S. Pat. No. 5,175,340; and Wang et. al. U.S. Pat. No. 5,830,441. Such sunscreen actives are added to the hair care or treatment compositions, especially those containing the aryl alkanone, in their conventional amounts and/or as directed by their manufacturers.

Having described the present invention in general terms, attention is now drawn to the following examples, which exemplify a number of the specific embodiments of the present invention and teachings.

Example 1: Computer Simulated Binding Energy Calculation with Transition Metals Using Quantum Mechanical Calculations One of the important goals in organometallic chemistry is to comprehensively study the interaction mechanism between the organic chelating ligands and metal ions. The interactions involving transition metal ions are particularly challenging because of hypervalency and subtle electronic properties. In this regard, quantum mechanical (QM) calculations emerged as a powerful complement to the experimental techniques such as X-ray crystallography, NMR and IR, by providing valuable structural and electronic details at the electronic structure level. Therefore, we have used QM calculations in order to identify and estimate the chelating properties of aryl alkanones of Formula 1. QM calculations demonstrated that the transition metal ions have the potential to dramatically influence the intrinsic conformation of the aryl alkanone compounds and form multi-dentate interactions with the carbonyl oxygen atoms of the aryl alkanones. Table 1 summarizes some of the results of this study.

As shown in Table 1, three moles of 1F or 1M or Deferiprone have the potential to coordinate all six coordination sites in $Fe^{3+}$, $Fe^{2+}$ and $Cu^{2+}$ as well as in $Zn^{2+}$. In fact, the results suggest that the aryl alkanones are either comparable or slightly better chelating agents than Deferiprone, a well-known and commercially available chelating agent used in pharmaceutical applications. The binding energy calculations also strongly suggest that aryl alkanones will be excellent selective chelators for Fe and Cu ions over Zn ions. As noted, 3 moles of aryl alkanones are needed to occupy all six co-ordination sites in $Fe^{3+}$, $Fe^{2+}$, $Cu^{2+}$ and $Zn^{2+}$ ions. These results also suggest that alteration of substituents in the aromatic ring will have minor effects in binding energies. Example 2 below experimentally confirms the suspected chelating ability of aryl alkanones.

TABLE 1

Computer simulated binding energy calculation between the present inventive ligand, Deferiprone, and transition metals

| Product | Binding Energy in kcal/mole | | | |
|---|---|---|---|---|
| | $Fe^{3+}$ | $Fe^{2+}$ | $Cu^{2+}$ | $Zn^{2+}$ |
| Compound 1F 3-(3,4,5-trimethoxy benzyl)-2,4-pentanedione | −1061.20 | −507.84 | −460.85 | −438.18 |
| Compound 1M (keto tautomer) 3-(3-methoxy-4-hydroxyl benzyl)-2,4-pentanedione | −1035.66 | −500.73 | −451.34 | −430.75 |
| Compound 1M (enol tautomer) | −1007.10 | −482.39 | Not Determined | −423.46 |
| Deferiprone | −1010.43 | −497.59 | −480.23 | −454.41 |

Example 2

A series of chelation studies were conducted in order to validate the chelation capabilities of the aryl alkanones as suggested by the computer simulation as well as compare those chelating abilities to the chelation of known chelators. The aryl alkanones tested were 3-(3,4-dimethoxy benzyl)-2,4-pentanedione (Compound 1D), 3-(4-methoxy benzyl)-2,4-pentanedione (Compound 1E), 3-(3,4,5-trimethoxy benzyl)-2,4-pentanedione (Compound 1F), 3-(3-methoxy-4-hydroxy benzyl)-2,4-pentanedione (Compound 1M) and 3-(3-methoxy-4-hydroxy benzyl)-4-ethylester-2-pentanone (Compound 2M). The known chelators tested were ethylenediamine tetraacetic acid (EDTA), ethylenediamine-N,N'-disuccinic acid (EDDS), Desferal, and Deferiprone. The test methodology employed generally followed that set forth in "Novel Fluorometric Assay for Hydroxyl Radical Prevention Capacity Using Fluorescein as the Probe", B Ou, M Hampsch-Woodill, J Flanagan, E K Deemer, R Prior, D Huang, J. Agric. Food Chem: 50(10); 2772-2777, 2002

The first chelation study (2A) evaluated the $Cu^{2+}$ chelation capability of the test and comparative chelators in the presence of excess $Ca^{2+}$. Here, a Fenton reaction was initiated with a mixture of $Cu^{2+}$, $CaCl_2$ and hydrogen peroxide at alkaline condition, the mixture comprising $[CuCl_2]$=200 μM, $[H_2O_2]$=0.055 μM, $[CaCl_2]$ 2.3 mM, and $[FL]$=6.20×10$^{-8}$ M. The test compounds were evaluated at a concentration of 600 μM for each of Compounds 1D, 1E and 1F and Deferiprone (a 3 molar excess) and 200 μM for each of EDDS and EDTA.

In general, oxidative damage is evidenced by the generation of hydroxyl radicals arising from the Fenton reaction, which generation is monitored by fluorescein (FL), a fluorescence probe sensitive to hydroxyl radicals. The loss of fluorescence intensity is an index of oxidation. Thus, the slower the fluorescence decay, the stronger the chelation for $Cu^{2+}$. As evident from Table 2A, the presence of Compounds 1D, 1E and 1F stopped or prevented the Fenton reaction from occurring indicating that $Cu^{2+}$ was almost completely chelated. Deferiprone demonstrated a moderate chelation capability, but, substantially less than the aryl alkanones, and the conventional chelators, EDTA and EDDS, demonstrated poor chelating capabilities.

A second chelation study (2B) was performed, similar to 2A with the one exception that no $CaCl_2$ was used: all other components remained the same. The results are summarized in the Table 2B. These results clearly demonstrated the superiority of Compounds 1D, 1E and 1F as compared to the commercial chelants, EDTA and EDDS as well as their comparable capabilities to Deferiprone in the absence of Ca. The fact that this study showed very little change in the fluorescence decay pattern of Compounds 1D, 1E and 1F with and without the ten-fold excess (relative to $Cu^{2+}$) of $CaCl_2$ evidences the selective chelating property of aryl alkanones to $Cu^{2+}$ over $Ca^{2+}$.

TABLE 2A $Cu^{2+}$ Chelation (with $CaCl_2$)

| | % Remaining of FL (20 min) | % Remaining of FL (40 min) | % Remaining of FL (80 min) |
|---|---|---|---|
| Blank | 72.6 | 46.9 | 22.2 |
| Compound 1D (Dimethoxy) | 97.2 | 96.0 | 96.5 |
| Compound 1E (Monomethoxy) | 98.6 | 96.9 | 96.3 |
| Compound 1F (Trimethoxy) | 96.0 | 94.4 | 92.7 |
| Compound 1M | 95.14 | 95.3 | 95.1 |
| Compound 2M | 99.9 | 98.3 | 100 |
| EDTA | 57.5 | 24.9 | 5.4 |
| EDDS | 78.5 | 56.4 | 30.4 |
| Deferiprone | 81.8 | 81.4 | 80.4 |

TABLE 2B $Cu^{2+}$ Chelation (no $CaCl_2$)

| | % Remaining of FL (20 min) | % Remaining of FL (40 min) | % Remaining of FL (80 min) |
|---|---|---|---|
| Blank | 61.1 | 29.7 | 13.8 |
| Compound 1D (Dimethoxy) | 96.9 | 94.8 | 86.9 |
| Compound 1E (Monomethoxy) | 99.8 | 99.8 | 99.0 |
| Compound 1F (Trimethoxy) | 97.0 | 94.8 | 87.7 |
| EDTA | 73.9 | 32.2 | 3.9 |
| EDDS | 91.1 | 81.9 | 62.9 |
| Deferiprone | 99.4 | 100 | 99.4 |

A third study (2C) was conducted to evaluate the chelating capabilities of the aryl alkanones as compared to the commercial chelants for chelating $Fe^{2+}$ ions. In this study, the same method employed in the second study (2B) was followed with the exception that $Fe^{2+}$ ions (200 μM) were employed rather than $Cu^{2+}$ ions. The results are summarized in the Table 2C Similar to their chelation capability for $Cu^{2+}$ ions, the aryl alkanones clearly demonstrated excellent chelation capability for $Fe^{2+}$ ions as compared to EDTA and Desferal. Additionally, although Deferiprone still provided good chelation capability, it was considerably less that attained by the aryl alkanones.

TABLE 2C

| | Fe$^{2+}$ Chelation | | |
|---|---|---|---|
| | % Remaining of FL (20 min) | % Remaining of FL (40 min) | % Remaining of FL (80 min) |
| Blank | 55.5 | 27.6 | 8.5 |
| Compound 1D | 98.3 | 98.3 | 98.3 |
| Compound 1E | 99.6 | 99.2 | 99.2 |
| Compound 1F | 98.6 | 98.1 | 97.7 |
| EDTA | 66.8 | 39.3 | 16.2 |
| Desferal | 79.8 | 50.4 | 19.3 |
| Deferiprone | 92.3 | 90.2 | 87.5 |

Finally, a fourth chelation study (2D) was performed in a manner similar to 2C with the exception that Fe$^{3+}$ ions were employed instead of the Fe$^{2+}$ ions. Results of this chelation study are summarized in the Table 2D. As before, the aryl alkanones performed superior to the conventional chelating agents. And, while EDTA and Desferal demonstrated moderate chelation capabilities for Fe$^{3+}$ ions, Deferiprone, which had shown moderate chelating capabilities for the previous ions tested, performed poorly with respect to Fe$^{3+}$ ions.

TABLE 2D

| | Fe$^{3+}$ Chelation | | |
|---|---|---|---|
| | % Remaining of FL (20 min) | % Remaining of FL (40 min) | % Remaining of FL (80 min) |
| Blank | 30.4 | 13.0 | 7.3 |
| Compound 1D | 99.6 | 99.6 | 99.2 |
| Compound 1E | 98.7 | 98.5 | 98.4 |
| Compound 1F | 88.9 | 86.5 | 84.4 |
| Compound 1M | 100 | 100 | 100 |
| Compound 2M | 99.8 | 99.3 | 98.5 |
| EDTA | 95.7 | 88.0 | 73.5 |
| Desferal | 81.9 | 74.1 | 68.7 |
| Deferiprone | 46.3 | 46.2 | 34.5 |

From the foregoing results, it is evident that the aryl alkanone compounds (1D, 1E and 1F) have little attraction for calcium and excellent, if not superior, chelating ability for copper as Cu$^{+2}$ and iron as Fe$^{+2}$ and Fe$^{+3}$, thereby rendering these ions unavailable for radical making. The lack of radicals results in a reduction in damage to hair fiber and the scalp normally attributable to such radicals. Additionally, the poor to moderate results manifested for the four commercially available chelating agents and the fact that no one commercial chelating agent showed even moderate chelating abilities for all ions clearly demonstrates superiority of the aryl alkanones and the fact that the current conventional chelating agents are not effective or marginally effective at best.

Example 3

A series of experiments was conducted to evaluate the ability of the aryl alkanones to quench singlet oxygen species as well as evaluate their stability in a singlet oxygen environment as compared to a conventional singlet oxygen quencher, αTocopherol.

The first study evaluated the quenching ability of the aryl alkanones versus αTocopherol. The test methodology employed is the method of W. Mullen et al., J of Agriculture & Food Chemistry, 59(9):3754-3762, 2011). The results are presented in Table 3A. As evident from Table 3A, the aryl alkanones demonstrated a markedly superior singlet oxygen quenching capability as compared to αTocopherol.

TABLE 3A

| | Singlet Oxygen Quenching | | | | |
|---|---|---|---|---|---|
| Compounds | α Tocopherol | Compd. 1F | Compd. 1D | Compd. 1E | Compd.1M |
| Antioxidant Power against singlet oxygen in μmole Trolox equivalent/g | 2,636 | 6,359 | 4,590 | 4,374 | 7,180 |

A second study was performed to determine the stability of the aryl alkanones and α tocopherol under a singlet oxygen environment. In this study, 5 ml of 1 mg/ml solution of each test compound (in DMSO) was mixed with 5 ml of a solution (pH 5) containing 0.16 mg/ml lithium molybdate, 4 ml 0.01 M NaOH, and 5 ml of 0.015% H$_2$O$_2$. 500 μl from each mixture was taken every 2 mins and added to 1 ml of 1 mg/ml curcumin solution (in DMSO) to stop the reaction. The mixture was then injected into an HPLC to monitor product degradation. The results are summarized in Table 3B and demonstrate the marked superior stability of the aryl alkanones as compared to the commonly use α tocopherol.

These two studies demonstrate that the aryl alkanones are more effective in quenching singlet oxygen than conventional antioxidants working by scavenging mechanism.

TABLE 3B

| | Stability under Singlet Oxygen Environment | | |
|---|---|---|---|
| Stability % Product remaining | α Tocopherol | Compd. 1F | Compd. 1M |
| 2 min | 73 | 92 | 95 |
| 4 min | 58 | 87 | 91 |
| 6 min | 47 | 85 | 88 |
| 8 min | 39 | 81 | 85 |
| 10 min | 35 | 80 | 82 |

Example 4: Hair Coloring Products

Several different kinds of hair coloring products are available for professional and consumer use including those that are applied as coloring shampoos and others as strict hair dyes. They are generally categorized as one of four types: permanent, demi-permanent, semi-permanent, and temporary. The permanent coloring lasts until the hair grows out, the demi-permanent lasts up to 24 washes, the semi-permanent lasts for six to eight weeks, and the temporary lasts for one to three washes. Demonstrating the breadth of the utility of the present teachings, the following exemplary hair care/coloring products containing the aryl alkanones are produced.

Permanent Hair Coloring

A typical permanent hair coloring product is formulated with two different components, a precursor-coupler base and an oxidizing base. The precursor-coupler base contains surfactants, alkaline or alkalizing agent, reducing agent, precursors, couplers, and water: an exemplary formulation is shown in Table 5A. The oxidizing base contains an oxidizing agent (e.g. peroxide), stabilizer for the peroxide, and surfactants as shown in Table 5B. Since the peroxide is unstable in alkaline solution, the precursor-coupler base and the oxidizing base have to be formulated separately for product storage and are only combined at the time of use.

TABLE 5A

Sample precursor-coupler base

Weight % of ingredient for desired hair color

| Ingredient | Dark brown | Light brown | Red | Black |
|---|---|---|---|---|
| Dodecyl benzene sulfonate (50%) | 14.0 | 14.0 | 14.0 | 14.0 |
| Cocodiethanolamide | 9.0 | 9.0 | 9.0 | 9.0 |
| Neodol 91-2.5 | 6.0 | 6.0 | 6.0 | 6.0 |
| Ammonium hydroxide | 6.0 | 6.0 | 6.0 | 6.0 |
| Sodium sulfite | 0.3 | 0.3 | 0.3 | 0.3 |
| p-Phenylenediamine | 0.4 | — | — | 0.4 |
| o-Aminophenol | 0.3 | 0.4 | — | 0.2 |
| p-Aminophenol | — | 0.4 | 0.4 | — |
| 4-Methyl-5-aminophenol | — | — | 0.4 | — |
| m-Aminophenol | — | — | — | 0.2 |
| Water | 64.0 | 63.9 | 63.9 | 63.9 |

TABLE 5B

Sample oxidizer base ingredients

| Ingredient | Weight % of ingredient |
|---|---|
| Hydrogen peroxide (30%) | 50.0 |
| Dodecyl benzene sulfonate (50%) | 33.0 |
| Phosphoric acid | 1.0 |
| Compound 1D or 1E or 1F | 0.1-1.0 |
| Water | 16.0 |

Demi-Permanent Hair Coloring

Demi-permanent hair coloring products are similar to permanent hair coloring products in terms of oxidative dyes but resemble the lasting properties of a semi-permanent hair color. The amount of peroxide is less and therefore offers less damage to the hair. An exemplary formulation is shown in Tables 6A and 6b, the latter comprising the oxidizing portion of the formulation.

TABLE 6A

Permanent Hair Dye Formula

| INCI Name | % w/w |
|---|---|
| Phase A-1 | |
| Water (demineralized) | QS |
| Glycerin | 3.00 |
| Sodium Sulfite | 0.20 |
| Resorcinol | 0.50 |
| Ethanolamine | 0.50 |
| Linoleamidopropyl PG- Dimonium Chloride Phosphate | 0.50 |
| Phase A-2 | |
| Carbomer | 0.40 |
| Polyquaternim –39 | 0.20 |
| Phase B | |
| Ammonium Hydroxide (50%) | 5.00 |
| Phase C | |
| Glyceryl Stearate | 2.50 |
| Cetearyl Alcohol | 3.00 |
| Sodium Laureth Sulfate | 2.00 |
| Octyldodecanol | 2.00 |
| Ceteareth-20 | 1.00 |

TABLE 6A-continued

Permanent Hair Dye Formula

| INCI Name | % w/w |
|---|---|
| Oleic Acid | 1.00 |
| Sodium Cetearyl Sulfate | 1.00 |
| Phase D | |
| m-Aminophenol | 0.75 |
| Sodium Sulfate | 0.25 |
| Toluene 2,5-Diamine Sulfate | 0.75 |
| 2-Amino-4-Hydroxyethylaminoanisole Sulfate | 0.10 |
| Phase F | |
| Citric Acid | QS |
| Benzoic Acid | 0.20 |
| Total | 100.00 |

*Chelating agent—aryl alkanone, e.g., Compound 1F or Compound 1M or Compound 2M. The aryl alkanones are preferably solubilized in PEG-300 or PEG-400 or PEG-400/water (1:1) for ease of formulating.

Post Treatment Products

Post treatment compositions are applied to hair following color treatment, especially during the period between color treatments, to enhance or protect the hair coloration and/or to provide further protection and/or reverse the damage to the hair caused by the hair coloring process and as supplemented by environmental damage and subsequent hair treatments such as shampooing, styling, etc. Table 7 presents an exemplary post treatment composition.

TABLE 6B

Cream Developer Formula

| INCI name | % w/w |
|---|---|
| Phase A-1 | |
| Water (demineralized) | QS |
| *Chelating agent | 0.1 to 0.3% |
| Propylene Glycol | 2.00 |
| Disodium Pyrophosphate | 0.20 |
| Etidronic Acid | 0.50 |
| 2,6-Dicarboxypyridine | 0.25 |
| Phase A-2 | |
| Hydrogen Peroxide | 5.00 |
| Phase B | |
| Potassium Hydroxide (50%) | 2.00 |
| Phase C | |
| Cetearyl Alcohol | 4.00 |
| Mineral Oil | 4.00 |
| Ceteareth-20 | 2.00 |
| Phase D | |
| Citric Acid | QS |
| Potassium Benzoate | 0.20 |
| Total | 100.00 |

These formulations are prepared according to conventional general methodologies which typically comprises individually preparing Phases A and B and then combining the two and allowing the combined formulation to hydrate. Separately Phase C is prepared and heated to 80° C. After fully hydrating the combination of Phases A and B are heated to 75° C. and Phase C is gradually added while mixing. The mixture is then cooled under propeller agitation until cooled to 40° C. Meanwhile, Phase D is separately prepared and, once the combination of Phase A, B and C is cooled, added to the mixture while maintaining mixing until uniform.

TABLE 7

Hair and Scalp Conditioner

| INCI name | % w/w |
|---|---|
| Phase A | |
| Water (demineralized) | 82.00 |
| Phase B | |
| Hydroxyethylcellulose | 1.00 |
| Glycerin | 2.00 |
| Cetrimonium Chloride | 0.50 |
| Phenoxyethanol | 1.00 |
| Potassium Sorbate | 0.25 |
| Phase C | |
| Glycery Stearate | 1.00 |
| Cetary Alcohol | 5.00 |
| Cetyl Esters | 0.50 |
| Behentrimonium Chloride | 1.00 |
| Isosorbide Dicaprylate | 2.00 |
| Caprylic/Capric Triglyceride | 0.50 |
| PEG-8 | 1.00 |
| *Compound. 1F or Compound 1D (present invention) | 0.50 |
| Phase D | |
| Panthenyl Hydroxypropyl Steardimonium Chloride | 0.30 |
| Panthenol | 0.30 |
| Hydrolyzed Rice Protein | 1.00 |
| Sodium Hydroxide | 0.15 |

*Chelating agent—aryl alkanone, e.g., Compound 1F or Compound 1D or Compound 1E. The aryl alkanones are preferably solubilized in PEG-300 or PEG-400 for ease of formulation.

Example 5: Sunscreen Spray

A sunscreen spray formulation is prepared for application to the hair to protect the color treated or bleached hair against sun-induced damage/color fading. An exemplary formulation is presented in Table 8 and is prepared by preparing Phase A and a pre-mix of Phase B, the latter being heated to 75° C. with mixing until it is completely free of solids. Phases A and C are then added to phase B at 50° C. with continued mixing. These sunscreen spray formulations are typically applied to hair that has been colored or to hair; however, they may also be applied as a general protectant for natural hair that has been or is to be exposed to damaging environmental conditions, as experience when swimming in a swimming pool.

TABLE 8

Broad spectrum clear spray sunscreen

| INCI name | Trade Name/Supplier | % w/w |
|---|---|---|
| Phase A | | |
| Ethanol | Ethanol | 39.00 |
| VA/Butyl Maleate/Isobornyl Acrylate Copolymer | Advantage Plus/Ashland | 2.00 |
| Phase B | | |
| Avobenzone | Eusolex 9020/EMD | 3.00 |
| Trimethoxybenzylidene Pentanedione* | Synoxyl ® HSS/Sytheon | 2.50 |
| Homosalate | Eusolex HMS/EMD | 10.00 |

TABLE 8-continued

Broad spectrum clear spray sunscreen

| INCI name | Trade Name/Supplier | % w/w |
|---|---|---|
| Octyl Salicylate | Eusolex OS/EMD | 5.00 |
| Compound 1D or 1E or 1F or 1M or 2M | Present inventive compounds | 1.00 |
| PEG-8 | PEG 400/Acme | 5.00 |
| Diisopropyl Adipate | Dermol DIA/Alzo | 5.00 |
| Phase C | | |
| Phenethyl Benzoate | X-tend 226/Ashland | 20.50 |
| C12-15 Alkyl Benzoate | Finsolv TN/Innospec | 5.00 |
| Isosorbide Dicaprylate | HydraSynol™ DOI/Sytheon | 2.00 |
| Total | | 100.00 |

*Trimethoxy benzylidene Pentanedione is as photostabilizer and in-vivo SPF booster. This can be replaced with Octocrylene or Diethylhexyl syringylidene malonate or Ethylhexyl methocycrylene

Example 6: Broad Spectrum Sunscreen Spray

A second, broad spectrum sunscreen spray formulation for the protection of color treated or bleached hair as well as the scalp against sun-induced damage is prepared. The formulation details are presented in Table 9. This product is produces in the same way as the preceding formulation.

TABLE 9

Broad spectrum clear spray sunscreen

| INCI name | Trade Name/Supplier | % w/w |
|---|---|---|
| Phase A | | |
| Ethanol | Ethanol | 39.00 |
| VA/Butyl Maleate/Isobornyl Acrylate Copolymer | Advantage Plus/Ashland | 2.00 |
| Phase B | | |
| Avobenzone | Eusolex 9020/EMD | 3.00 |
| Trimethoxybenzylidene Pentanedione | Synoxyl ® HSS/Sytheon | 2.50 |
| Homosalate | Eusolex HMS/EMD | 10.00 |
| Octyl Salicylate | Eusolex OS/EMD | 5.00 |
| Compound 1F or 1D or 1E or 1M or 2M | Present inventive compounds | 1.00 |
| PEG-8 | PEG 400/Acme | 8.00 |
| Diisopropyl Adipate | Dermol DIA/Alzo | 2.00 |
| Phase C | | |
| Phenethyl Benzoate | X-tend 226/Ashland | 20.50 |
| C12-15 Alkyl Benzoate | Finsolv TN/Innospec | 5.00 |
| Isosorbide Disunflowerseedate | HydraSynol™ IDL/Sytheon | 2.00 |
| Total | | 100.00 |

Example 7: Dry & Wet Hair Combing

In order to demonstrate the effect of the aryl alkanones as a preventative/reparative ingredient for hair coloring products, a series of tests were performed in which a plurality of hair tresses each weighing approximately 3 g and measuring 8" in length and 1" in width (from International Hair Importers & Products—Glendale, N.Y.) were bleached using a standard protocol. Thirty-two (32) of the hair tresses were then dyed using a commercial hair coloring product (Revlon ColorSilk (ammonia-free) #43 Medium Golden Brown for Colorant and Developer) with half of those tresses being colored with the hair coloring product as is (Colored) and the other half being colored with the hair coloring product to which 0.5% by wt. of Comp 1F (as a 20% solution inPEG-400) was added to the colorant (the "Modified Colored"). Coloring was performed in accordance with the manufacturer's directions. After dyeing, the hair tresses were allowed to stand for 30 min before any further processing. Thereafter one half (8) of the Colored and one half (8) of the Modified Colored tresses were dried for the same period of time under the same drying conditions.

All of the hair tresses, wet and dry, were then subjected to combability testing to assess the combing force needed to comb through the hair. Combing forces were determined using an Instron tensile tester to measure frictional forces while a hair tress is pulled through a comb in accordance with the widely-used method of Garcia & Diaz (JSCC, 27, (1976) 379-398—Combability Measurements on Hair). Six combing strokes were performed per tress with eight replicate hair tresses for each test to ensure statistical relevance. JMP™ analytical software was used to perform the statistical analysis. Statistics were performed using the student's t-test at the 95% confidence level.

The results of the wet combing test are shown in Table 10 and the results of the dry combing test are shown in Table 11.

TABLE 10

| Wet Combing | | | | |
|---|---|---|---|---|
| Treatment | | Number | Mean (gf) | Standard Deviation | Standard Error Mean |
| Colored | Baseline-1 | 8 | 107.21 | 19.99 | 7.07 |
|  | Control | 8 | 107.54 | 20.87 | 7.38 |
| Modified | Baseline-2 | 8 | 97.32 | 16.26 | 5.75 |
| Colored | Invention | 8 | 77.60* | 11.13 | 3.93 |

*Statisticaly significant (p = 0.05)

TABLE 11

| Dry Combing** | | | | |
|---|---|---|---|---|
| Treatment | | Number | Mean | Standard Deviation | Standard Error Mean |
| Colored | Baseline-1 | 7 | 138.9 | 57.52 | 20.34 |
|  | Control-1 | 7 | 67.2*+ | 10.47 | 3.70 |
| Modified | Baseline-2 | 7 | 148.1 | 39.12 | 13.86 |
| Colored | Invention | 7 | 51.5*+ | 34.87 | 12.33 |

**Note:
only seven replications were used in setting forth the final results as one tress in each series provided a clearly anomalous result, warranting its exclusion.
*+Statistically significant p = <0.05

As seen from Table 11, there is a significant decrease in dry combing forces for both the Colored and Modified Colored hair tresses over their respective baselines. Also, there is a significant difference between combing forces for the Modified Colored and Colored hair tresses as well.

Based on the results presented in Tables 10 and 11, it is clear that the aryl alkanone compound provided a lubriciousness and/or silkiness to the hair and/or reduced tangles in the hair as evidenced by the much lower, markedly lower in the wet comb test, combing forces. These results are consistent with the manifestation of less damage to and friction on the hair, thereby facilitating manageability and providing detangling benefits.

Similar experiments are contemplated with Compound 1D and Compound 1E with the expectation of similar results.

Example 8

A further experiment was conducted to assess the impact of the use of hair care products containing the select aryl alkanones on hair which has been colored, particularly with respect to color fading. Such issues are well known and reported on, e.g., B Locke and J Jachowicz, Fading of artificial hair color and its prevention by photofilters, *J Cosmet Sci*, 56 407-425 (2005).

In this experiment, bleached European brown hair tresses were dyed with a commercially available medium auburn color for 30 min following the instructions provided in color kits (Revlon color kit). For testing of UVB damage, virgin dark brown hair was used. A number of the tresses were treated with a standard shampoo and conditioner whereas a second number were treated with the same except that Compound 1F was added to each. A subset of the treated tresses were then irradiated for 3 hr on each side, totaling 6 hr-equivalent to one day of UV exposure with UV radiation (200-400 nm) at 50 W/m1 using a quartz inner filter and type "s" borosilicate outer filter. At the start of the study and at intervals equivalent to every five days of UV exposure (which is after every 30 hours), tresses were treated again with the Compound 1F modified and the unmodified shampoos and conditioners. Irradiated tresses were exposed to the total equivalent of 15 days of UV exposure. Test conditions were maintained at 40° C. and 65% relative humidity. Different types of tresses were compared, including those that were dyed and not exposed to treatment or UV exposure; dyed and treated with the control shampoos and conditioners and exposed to UV; and dyed and treated with shampoos and conditioners containing the Compound 1F and exposed to UV. Comparative color loss was determined both objectively and subjectively. The total color loss ($\Delta E$) was calculated by assessing the changes in L*, a*, b* readings. The changes in hair color indexes were calculated using the respective values after the shampoo and conditioner treatments and before UV exposure; and after the equivalent of 15 days of UV exposure. The results of the instrumental evaluations were confirmed via subjective testing.

Based on the objective testing, the total color change of the medium brown-colored hair treated with the modified and unmodified shampoos and conditioners after 15 days of UV exposure was as follows:

$\Delta E$ control—10.46

$\Delta E$ Compound 1F or 1D—7.28

The swatches were photographed and compared to dyed but untreated swatches, which represent the initial dye color, to allow for visual comparisons. Panelists were also asked to rate the color protection effects in simple comparisons of the control and the Compound 1F swatches to the untreated control. The panel evaluation demonstrated a strong correlation between the visual results and the instrumental results. On medium brown hair, 95.1% of panelists chose the tresses treated with the Compound 1F shampoo as having retained the most color. Accordingly, these results show that the aryl alkanones also prevent/reduce hair color degradation of colored hair, especially that which is induced by sun-induced photodegradation.

Example 9: Ethnic Hair Relaxer & Shampoo

To further demonstrate the breadth of the benefits attainable with the practice of the present invention, hair samples were treated with a commercial hair relaxer product (Dark and Lovely Beautiful Beginnings No-Mistake Smooth Relaxer for All Hair Types) This product has four components: 1) the Hair and Scalp Protective Gel comprising Paraffinum Liquidum (Mineral Oil), Diethylhexyl Maleate, Isoprene Copolymer, Hydrogenated Styrene, and Butadiene Copolymer; 2) the No-Mistake Relaxer Cream comprising water, Petrolatum, Paraffinum Liquidum (Mineral Oil), Cetearyl Alcohol, Guanidine Carbonate, PEG-75 Lanolin, Behentrimonium Methosulfate, Polyquaternium-6, Isopropyl Myristate, Isopropyl Palmitate, CI 15510 (Orange 4), Denatonium Benzoate, Aloe Barbadensis Leaf Extract, Aloe Barbadensis Extract; 3) the No-Mistake Cream Activator Propylene Glycol, Calcium Hydroxide, Silica, CI 77891 (Titanium Dioxide); and 4) the Color Signal Neutralizing Shampoo comprising water, Sodium Laureth Sulfate, Polysorbate 21, PPG-5-Ceteth-10 Phosphate, Cocamidopropyl Betaine, Salicylic Acid, Polysorbate 20, Polyquaternium-7, Sodium Chloride, Hexylene Glycol, Sodium Hydroxide, Hydroxypropyltrimonium Honey, Phenolsulfonephthalein, Citric Acid; and the Deep Conditioner comprising water Propylene Glycol, Cetearyl Alcohol, Polyquaternium-37, Propylene Glycol Dicaprylate, Dicaprate, Behentrimonium Methosulfate, Sodium Benzoate, PPG-1 Trideceth-6, Stearyl Dimethicone, Chlorhexidine Dihydrochloride, 2-Oleamido-1,3-Octadecanediol.

The commercial product was used as instructed except that a number of the hair tresses were treated with the commercial product modified by adding Compound 1F to the relaxer and/or Compound 1F to the shampoo. In both instances, the amount of Compound 1F added was 0.5 g and was added as a 20% solution of Compound 1F in PEG400

As with the previous example, hair tresses were evaluated by a panel of six individuals and rated based upon coarseness, smoothness, etc. as manifested by easy of combing. Ratings were based upon a sliding scale wherein "+" represented the baseline before treatment of the hair, "++" represented very minor damage with minimal tangles, "+++" represented moderately damaged hair with moderate tangling, and "++++" represented severely damaged hair with significant tangling. The results are presented in Table 10.

TABLE 12

Relaxer Evaluation

| Resultse | Baseline Before treatment | Control Commercial product used as-is | Modified 1 Compound 1 F or Compound 1D added to relaxer | Modified 2 Compound 1F or Compound 1D added to shampoo |
|---|---|---|---|---|
| Evaluation by panelists (6) | + | ++++ | ++ | ++ |

As noted in Table 12, the panel evaluation concluded that the addition of the aryl alkanone Compound 1F or 1D to the relaxer and shampoo markedly reduced the damage caused by the use of the same product without Compound 1F. In this study, more than 80% of the panelists characterized the hair treated with the Compound 1F or 1D shampoo or relaxer as being very smooth in appearance and silky to the touch.

The patents, patent publications and other documents cited herein, including any cross-referenced or related patent or patent applications, are hereby incorporated herein by reference in their entirety unless expressly excluded or otherwise limited. The citation of any document is not an admission that it is pertinent prior art with respect to any invention disclosed or claimed herein or that it alone, or in combination with any other citation or combination of citations, teaches, suggests or discloses any such invention. Further, to the extent that any meaning or definition expressly applied to a term in this document conflicts with any meaning or definition of the same term in a document incorporated by reference, the meaning or definition assigned to that term in this document shall govern.

The various embodiments described above are provided by way of illustration only and should not be construed as or deemed to limit the claims attached hereto. The present invention can suitably comprise, consist of, or consist essentially of, any of the disclosed or recited elements. Thus, the invention illustratively disclosed herein can be suitably practiced in the absence of any element, which is not specifically disclosed as being required herein. Furthermore, various modifications and changes to the teachings herein will be recognized by those skilled in the art having the benefit of the present teachings and may be made to the present teachings without departing from the true spirit and scope of the invention as claimed and are, hence, deemed and to be deemed within the full scope of the appended claims.

I claim:

1. An improved hair care composition wherein the improvement comprises the presence of an effective amount of at least one aryl alkanone compound having the Formula I

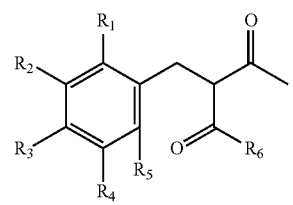

wherein $R_1$, $R_2$, $R_3$, $R_4$ and $R_5$ which may be the same or different, are each independently H, OH, or a $C_1$-$C_8$ linear or branched alkyl or alkoxy group, and $R_6$ is $CH_3$ to prevent or reduce hair damage or hair color fading as compared to the use of the same composition without the aryl alkanone wherein the effective amount of the aryl alkanone compound is characterized as being present at a weight ratio of from 25:1 to 1:25 based on the amount of oxidizing agents in the case of hair care composition including an oxidizing agent or to be used concurrent with an oxidizing agent containing hair care composition; otherwise the effective amount is from about 0.1 to 15 percent by weight based on the total weight of the hair care composition.

2. The improved hair care composition of claim 1 wherein $R_1$, $R_2$, $R_3$, $R_4$ and $R_5$ which may be the same or different, are each independently H or a $C_1$-$C_6$ linear or branched alkyl or alkoxy group.

3. The improved hair care composition of claim 1 wherein $R_1$, $R_2$, $R_3$, $R_4$ and $R_5$ which may be the same or different, are each independently H or a $C_1$-$C_4$ linear or branched alkyl or alkoxy group.

4. The improved hair care composition of claim 1 wherein $R_1$=$R_5$=H and each of $R_2$, $R_3$, and $R_4$ is independently a $C_1$-$C_4$ linear or branched alkoxy or a $C_1$-$C_8$ linear or branched alkyl.

5. The improved hair care composition of claim 1 wherein $R_1=R_2=R_5=H$; and each of $R_3$ and $R_4$ is independently a $C_1$-$C_4$ linear or branched alkoxy or $C_1$-$C_8$ linear or branched alkyl.

6. The improved hair care composition of claim 1 wherein the aryl alkanone of Formula 1 is selected from the group consisting of:
Compound 1A: $R_1=R_3=R_5=$OMe and $R_2=R_4=H$; $R_6=CH_3$;
Compound 1B: $R_1=R_3=R_5=H$ and $R_2=R_4=$OMe; $R_6=CH_3$;
Compound 1C: $R_1=R_2=R_5=H$ and $R_3=R_4=$Me; $R_6=CH_3$;
Compound 1D: $R_1=R_2=R_5=H$ and $R_3=R_4=$OMe; $R_6=CH_3$;
Compound 1E: $R_1=R_2=R_4=R_5=H$; $R_3=$OMe; $R_6=CH_3$;
Compound 1F: $R_1=R_5=H$; $R_2=R_3=R_4=$OMe; $R_6=CH_3$;
Compound 1G: $R_1=R_5=H$; $R_2=R_3=R_4=$Me; $R_6=CH_3$;
Compound 1H: $R_1=R_4=$OMe; $R_2=R_3=R_5=H$; $R_6=CH_3$;
Compound 1I: $R_1=R_3=R_5=H$; $R_2=R_4=$Me; $R_6=CH_3$;
Compound 1J: $R_1=R_2=R_4=R_5=H$; $R_3=$Me; $R_6=CH_3$;
Compound 1K: $R_1=R_3=R_4=R_5=H$; $R_2=$Me; $R_6=CH_3$;
Compound 1L: $R_1=R_3=R_4=R_5=H$; $R_2=$OMe; $R_6=CH_3$;
Compound 1M: $R_1=R_2=R_5=H$; $R_3=$OH; $R_4=$OCH$_3$; $R_6=CH_3$;
Compound 1N: $R_1=R_3=R_5=H$; $R_2=R_4=$Me; $R_6=CH_3$;
Compound 1P: $R_1=R_2=R_4=R_5=H$; $R_3=$Me; $R_6=CH_3$; and
Compound 1Q: $R_1=R_2=R_4=R_5=H$; $R_3=$OMe; $R_6=CH_3$.

7. The improved hair care composition of claim 1 wherein the hair care composition comprises other agents or ingredients which are oxidizing agents and the one or more aryl alkanones is present in an amount whereby the weight ratio of the aryl alkanone to the oxidizing agents is from 25:1 to 1:25.

8. The improved hair care composition of claim 1 wherein the hair care composition comprises other agents or ingredients which are oxidizing agents and the one or more aryl alkanones is present in an amount whereby the weight ratio of the aryl alkanone to the oxidizing agents is from 15:1 to 1:15.

9. The improved hair care composition of claim 1 wherein the hair care composition is a hair treatment composition selected from hair coloring products, shampoos, conditioners, hair restorative treatments, perming products, alcohol based hair sprays, gel hair sprays, and hair bleaching compositions.

10. The improved hair care composition of claim 1 wherein the hair care composition is a hair coloring product which comprises one or more components that are individually packaged and combined and/or used concurrently or sequentially in the hair coloring process and the aryl alkanone is present in at least one of the components thereof.

11. The improved hair care composition of claim 1 wherein the aryl alkanone is free of phenolic hydroxy groups.

12. The improved hair care composition of claim 1 wherein the composition is a pretreatment composition or a post treatment composition and the composition comprises from about 0.1 to about 15 wt percent of the aryl alkanone.

13. The improved hair care composition of claim 1 wherein the composition is a pretreatment composition or a post treatment composition and the composition comprises from about 0.5 to about 10 wt percent of the aryl alkanone.

14. The improved hair care composition of claim 1 wherein the composition is a pretreatment composition or a post treatment composition and the composition comprises from about 1 to about 4 wt percent of the aryl alkanone in a carrier suitable for application to the hair.

15. The improved hair care composition of claim 1 wherein the aryl alkanone compound is acetyl zingerone.

16. The improved hair care composition of claim 1 wherein at east one of $R_2$, $R_3$, and $R_4$ is a $C_1$-$C_8$ linear or branched alkoxy or alkyl.

17. A method of preventing or protecting hair from photo-, thermal- or oxidative damage comprising applying to the hair a composition comprising an effective amount of at least one aryl alkanone compound having the Formula I

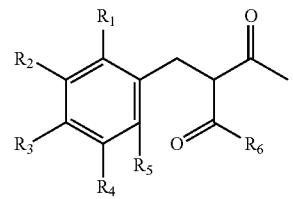

wherein $R_1$, $R_2$, $R_3$, $R_4$ and $R_5$ which may be the same or different, are each independently H, OH, or a $C_1$-$C_8$ linear or branched alkyl or alkoxy group, and $R_6$ is $CH_3$ prior to exposing the hair to conditions which effect or promote photo-, thermal- or oxidative damage, whereby less hair damage is found as compared to the hair exposed to those conditions without the application of the composition wherein the effective amount of the aryl alkanone compound is characterized as being from about 0.1 to 15 percent by weight of the composition.

18. A method of reducing the damage caused by hair treatment compositions comprising either (i) incorporating into the hair treatment composition an effective amount of at least one aryl alkanone compound having the Formula I

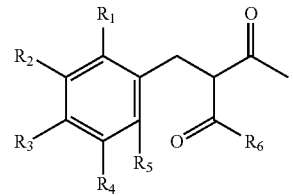

wherein $R_1$, $R_2$, $R_3$, $R_4$ and $R_5$ which may be the same or different, are each independently H, OH, or a $C_1$-$C_8$ linear or branched alkyl or alkoxy group, and $R_6$ is $CH_3$ prior to or concurrent with its application to the hair or (ii) treating the hair with a composition comprising at least one of the aforementioned aryl alkanones in an effective amount prior to or following the application of the hair treatment composition to the hair, whereby less hair damage is found as compared to the treated hair which has not also been treated with the aryl alkanone wherein the effective amount of the aryl alkanone compound is characterized as being present at a weight ratio of from 25:1 to 1:25 based on the amount of oxidizing agents in the case of hair care composition including an oxidizing agent or to be used concurrent with an oxidizing agent containing hair care composition; otherwise, the effective amount is from about 0.1 to 15 percent by weight based on the total weight of the hair care composition.

19. The method of claim 18 wherein the composition containing the aryl alkanone is applied to the hair prior to application of a hair treatment composition comprising oxidizing agents.

20. The method of claim 18 wherein the composition containing the aryl alkanone is applied before bleaching, perming or coloring the hair.

21. The method of claim 18 wherein the composition containing the aryl alkanone is applied to the hair prior to exposure to oxidizing conditions other than a hair treatment composition.

22. The method of claim 21 wherein the composition containing the aryl alkanone is applied prior to exposure to the sun or air pollutants and/or prior to participation in an aquatic activity in which the hair is exposed to water chemicals.

23. The method of claim 18 wherein the composition containing the aryl alkanone is applied to the hair following the treatment of the hair with a hair treatment composition comprising oxidizing agents.

24. The method of claim 18 wherein the composition containing the aryl alkanone is applied to the hair following exposure to oxidizing conditions other than a hair treatment composition.

25. The method of claim 24 wherein the composition containing the aryl alkanone is applied to the hair following exposure to the sun or air pollutants and/or participation in an aquatic activity in which the hair is exposed to water chemicals.

26. The method of claim 17 wherein the aryl alkanone compound is acetyl zingerone.

27. The method of claim 18 wherein the aryl alkanone compound is acetyl zingerone.

28. The method of claim 17 wherein at least one of $R_2$, $R_3$, and $R_4$ is a $C_1$-$C_8$ linear or branched alkoxy or alkyl.

29. The method of claim 18 wherein at east one of $R_2$, $R_3$, and $R_4$ is a $C_1$-$C_8$ linear or branched alkoxy or alkyl.

30. The method of claim 17 wherein the aryl alkanone of Formula 1 is selected from the group consisting of:
Compound 1A: $R_1=R_3=R_5=$OMe and $R_2=R_4=$H; $R_6=CH_3$;
Compound 1B: $R_1=R_3=R_5=$H and $R_2=R_4=$OMe; $R_6=CH_3$;
Compound 1C: $R_1=R_2=R_5=$H and $R_3=R_4=$Me; $R_6=CH_3$;
Compound 1D: $R_1=R_2=R_5=$H and $R_3=R_4=$OMe; $R_6=CH_3$;
Compound 1E: $R_1=R_2=R_4=R_5=$H; $R_3=$OMe; $R_6=CH_3$;
Compound 1F: $R_1=R_5=$H; $R_2=R_3=R_4=$OMe; $R_6=CH_3$;
Compound 1G: $R_1=R_5=$H; $R_2=R_3=R_4=$Me; $R_6=CH_3$;
Compound 1H: $R_1=R_4=$OMe; $R_2=R_3=R_5=$H; $R_6=CH_3$;
Compound 1I: $R_1=R_3=R_5=$H; $R_2=R_4=$Me; $R_6=CH_3$;
Compound 1J: $R_1=R_2=R_4=R_5=$H; $R_3=$Me; $R_6=CH_3$;
Compound 1K: $R_1=R_3=R_4=R_5=$H; $R_2=$Me; $R_6=CH_3$;
Compound 1L: $R_1=R_3=R_4=R_5=$H; $R_2=$OMe; $R_6=CH_3$;
Compound 1M: $R_1=R_2=R_5=$H; $R_3=$OH; $R_4=$OCH$_3$; $R_6=CH_3$;
Compound 1N: $R_1=R_3=R_5=$H; $R_2=R_4=$Me; $R_6=CH_3$;
Compound 1P: $R_1=R_2=R_4=R_5=$H; $R_3=$Me; $R_6=CH_3$; and
Compound 1Q: $R_1=R_2=R_4=R_5=$H; $R_3=$OMe; $R_6=CH_3$.

31. The method of claim 18 wherein the aryl alkanone of Formula 1 is selected from the group consisting of:
Compound 1A: $R_1=R_3=R_5=$OMe and $R_2=R_4=$H; $R_6=CH_3$;
Compound 1B: $R_1=R_3=R_5=$H and $R_2=R_4=$OMe; $R_6=CH_3$;
Compound 1C: $R_1=R_2=R_5=$H and $R_3=R_4=$Me; $R_6=CH_3$;
Compound 1D: $R_1=R_2=R_5=$H and $R_3=R_4=$OMe; $R_6=CH_3$;
Compound 1E: $R_1=R_2=R_4=R_5=$H; $R_3=$OMe; $R_6=CH_3$;
Compound 1F: $R_1=R_5=$H; $R_2=R_3=R_4=$OMe; $R_6=CH_3$;
Compound 1G: $R_1=R_5=$H; $R_2=R_3=R_4=$Me; $R_6=CH_3$;
Compound 1H: $R_1=R_4=$OMe; $R_2=R_3=R_5=$H; $R_6=CH_3$;
Compound 1I: $R_1=R_3=R_5=$H; $R_2=R_4=$Me; $R_6=CH_3$;
Compound 1J: $R_1=R_2=R_4=R_5=$H; $R_3=$Me; $R_6=CH_3$;
Compound 1K: $R_1=R_3=R_4=R_5=$H; $R_2=$Me; $R_6=CH_3$;
Compound 1L: $R_1=R_3=R_4=R_5=$H; $R_2=$OMe; $R_6=CH_3$;
Compound 1M: $R_1=R_2=R_5=$H; $R_3=$OH; $R_4=$OCH$_3$; $R_6=CH_3$;
Compound 1N: $R_1=R_3=R_5=$H; $R_2=R_4=$Me; $R_6=CH_3$;
Compound 1P: $R_1=R_2=R_4=R_5=$H; $R_3=$Me; $R_6=CH_3$; and
Compound 1Q: $R_1=R_2=R_4=R_5=$H; $R_3=$OMe; $R_6=CH_3$.

* * * * *

UNITED STATES PATENT AND TRADEMARK OFFICE
CERTIFICATE OF CORRECTION

PATENT NO. : 11,077,035 B2
APPLICATION NO. : 16/059425
DATED : August 3, 2021
INVENTOR(S) : Ratan K. Chaudhuri It is certified that error appears in the above-identified patent and that said Letters Patent is hereby corrected as shown below:

In the Claims

At Column 34, Line 17 the word "east" should be --least--.

Signed and Sealed this
Twenty-first Day of May, 2024

Katherine Kelly Vidal
*Director of the United States Patent and Trademark Office*